United States Patent
Oh

(10) Patent No.: US 9,273,116 B2
(45) Date of Patent: Mar. 1, 2016

(54) FUSION PROTEIN COMPRISING ALBUMIN AND RETINOL-BINDING PROTEIN

(75) Inventor: Jun Seo Oh, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 69 days.

(21) Appl. No.: 14/002,034

(22) PCT Filed: Feb. 28, 2012

(86) PCT No.: PCT/KR2012/001497
§ 371 (c)(1),
(2), (4) Date: Aug. 28, 2013

(87) PCT Pub. No.: WO2012/118323
PCT Pub. Date: Sep. 7, 2012

(65) Prior Publication Data
US 2013/0338074 A1 Dec. 19, 2013

(30) Foreign Application Priority Data
Feb. 28, 2011 (KR) ........................ 10-2011-0018074

(51) Int. Cl.
*C07K 14/76* (2006.01)
*C07K 14/47* (2006.01)
*A61K 38/00* (2006.01)

(52) U.S. Cl.
CPC ............. *C07K 14/76* (2013.01); *C07K 14/4702* (2013.01); *A61K 38/00* (2013.01); *C07K 2319/00* (2013.01); *C07K 2319/31* (2013.01)

(58) Field of Classification Search
CPC .... A61K 38/00; C07K 14/4702; C07K 14/76; C07K 2319/00; C07K 2319/31
See application file for complete search history.

(56) References Cited

U.S. PATENT DOCUMENTS 6,051,692 A * 4/2000 Bandman et al. ............. 530/350

FOREIGN PATENT DOCUMENTS

EP 2 277 889 A2 1/2011
WO WO 2011015634 A2 * 2/2011 ............. A61K 38/00

OTHER PUBLICATIONS

UniProt Protein Database, Protein Accession P02768, Serum Albumin, Accessed on May 29, 2015.*
Nayoung Kim et al. "Formation of vitamin A lipid droplets in pancreatic stellate cells requires albumin" GUT vol. 58, pp. 1382-1390; Published online Mar. 16, 2009; abstract in English.
Soyoung Choi, et al; "Recombinant fusion protein of albumin-retinol binding protein inactivates stellate cells", Biochemical and Biophysical Research Communications vol. 418, pp. 191-197; Available online Jan. 12, 2012.
Nayoung Kim, et al; "Albumin mediates PPAR-γ or C/EBP-α-induced phenotypic changes in pancreatic stellate cells", Biochemical and Biophysical Research Communications, vol. 391, pp. 640-644; Available online Nov. 22, 2009.
Martin Roderfeld, et al; "Inhibition of hepatic fibrogenesis by matrix metalloproteinase-9 mutants in mice", The FASEB Journal, vol. 20(3); pp. 444-454; Mar. 2006.
Bernd Schnabl, et al; "A TLR4/MD2 fusion protein inhibits LPS-induced pro-inflammatory signaling in hepatic stellate cells". Biochemical and Biophysical Research Communications, vol. 375, pp. 210-214; Available online Jul. 23, 2008.
Wonbaek Yoo, et al; "Albumin expression is required for adipocyte differentiation of 3T3-L1 cells", Biochemical and Biophysical Research Communications, vol. 397, pp. 170-175; Available online Jun. 1, 2010.
Extended European Search Report dated Aug. 1, 2015; Appln. No. 12752190.4-1410/ 2682406 PCT/KR2012001497.

* cited by examiner

*Primary Examiner* — James H Alstrum Acevedo
*Assistant Examiner* — Erinne Dabkowski
(74) *Attorney, Agent, or Firm* — Ladas & Parry LLP

(57) ABSTRACT

There is provided a fusion protein comprising albumin and retinol-binding protein, which can be used for preventing or treating fibrotic diseases. The fusion protein, in which albumin and a retinol-binding protein (RBP) are bound together, induces the formation of cytoplasmic lipid droplets in stellate cells and returns the shape of activated stellate cells to the previous shape thereof before activation. Therefore, the fusion protein can be effectively used in preventing or treating fibrotic diseases occurring in the liver, pancreas, lungs, or other organs.

13 Claims, 8 Drawing Sheets

FIG. 3
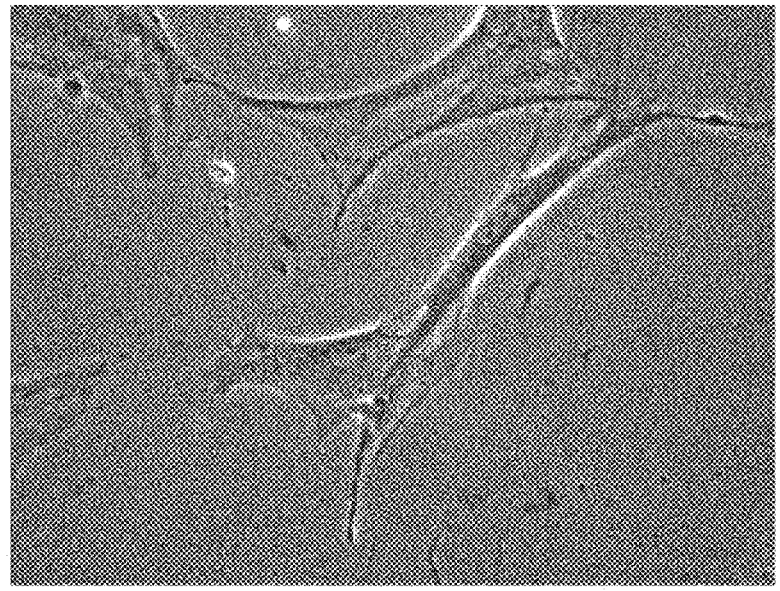
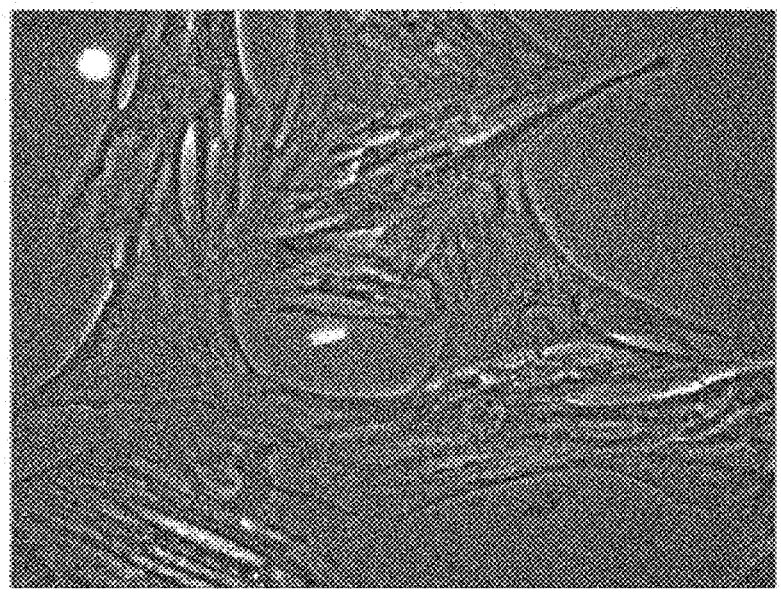

FIG. 8
A
UUO-induced renal fibrosis
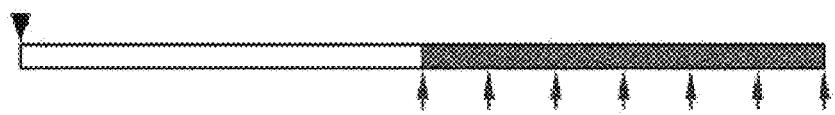
▼ UUO (unilateral ureteral obstruction)
saline or R-III injection (i.v.)
B
MT
control
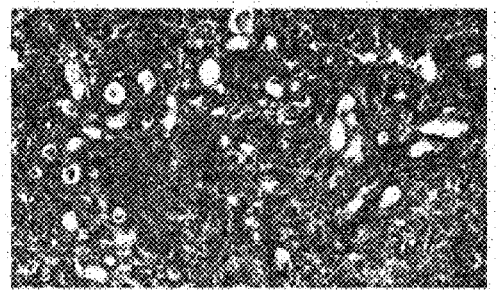
R-III
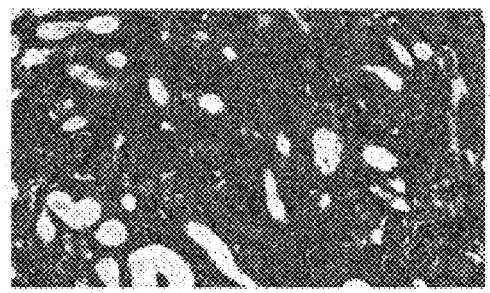

FUSION PROTEIN COMPRISING ALBUMIN AND RETINOL-BINDING PROTEIN

TECHNICAL FIELD

The present invention relates to a fusion protein comprising albumin and retinol-binding protein, which is capable of being used for preventing or treating fibrotic diseases occurring in the liver, pancreas, lungs, or other organs.

BACKGROUND ART

Tissue fibrosis leads to fatal defunctionalization of tissues. For example, liver fibrosis leads to defunctionalization of the liver, and subsequently progresses to hepatocirrhosis or liver cancer, and pancreas fibrosis is commonly observed in cases of chronic pancreatitis or pancreatic cancer. Nevertheless, up to now, there have been no drugs for treating the fibrosis, and tissue grafting is the only effective cure. The reason that there are no drugs for treating the fibrosis is because molecular mechanism of tissue fibrosis has not been identified.

Recently, it has been found that tissue fibrosis is caused by activating stellate cells, which are one type of cell constituting tissues, and thus excessively expressing and accumulating an extracellular matrix such as collagen. It has been reported that the stellate cells become distributed in the pancreas, lungs, kidneys, and intestines, in addition to the liver.

The stellate cells play a key role in controlling retinoid homeostasis in the whole body. Vitamin A (retinol) acquired from diet is bound to retinol-binding protein (RBP) in blood flow; circulated, transferred to the stellate cells through STRA6 as a RBP receptor, and then stored as retinyl ester in cytoplasmic fat droplets. The present inventors disclosed that albumin that is expressed in the stellate cells and has intact fatty acid binding sites is involved in formation of vitamin A—containing fat droplets, inhibits activation of the stellate cells, and returns albumin expressed in the activated stellate cells to its previous state before activation (Non-Patent Document 1: Kim N, Yoo W, Lee J, Kim H, Lee H, Kim Y, Kim D, Oh J.* (2009) Formation of vitamin A fat droplets in pancreatic stellate cells requires albumin. Gut 58(10), 1382-90; Non-Patent Document 2: Kim N, Choi S, Lim C, Lee H, Oh J. (2010) Albumin mediates PPAR-g and C/EBP-a-induced phenotypic changes in pancreatic stellate cells. Biochem. Biophys. Res. Commun. 391(1), 640-44.)

DISCLOSURE

Technical Problem

An object of the present invention is to treat fibrotic diseases by inhibiting activation of stellate cells through increasing the levels of albumin in the stellate cells, returning the activated stellate cells to the state of the previous stellate cells before activation, or inducing aging of the stellate cells.

Technical Solution

In order to achieve the above object, an exemplary embodiment of the present invention provides a fusion protein comprising albumin and a retinol-binding protein.

Albumin is a multifunctional plasma protein that is primarily synthesized by liver cells. Albumin has three domains, each of which consists of two small sub-domains: A and B. It is known that albumin plays a role in molecular migration by wrapping around hydrophobic substances including fatty acids, and then carrying the hydrophobic substances including fatty acids in the blood. According to a crystallographic analysis, five principal fatty acid binding sites are asymmetrically distributed within the albumin (one in sub-domain IB, one between IA and IIA, two in IIIA, and one in IIIB).

The present inventors hypothesized that albumin expressed in stellate cells may promote formation of intracellular fat droplets by stabilizing storage of retinyl ester. On the other hand, the present inventors noticed that a retinol-RBP complex prepared by combining retinol with a RBP receptor in the stellate cells may be internalized into a cell by endocytosis. In reference to this point, an expression vector encoding a fusion protein including albumin and a retinol-binding protein (RBP) was prepared in order to increase a level of albumin in the stellate cells, and then an effect according to the expression of the fusion protein was tested. As a result, with the wild-type albumin, the expression of recombinant fusion protein induced the formation of fat droplets in the stellate cells, and led to the phenotype reversion of activated stellate cells into quiescent cells. In addition, levels of α-SMA, an activation marker of stellate cells, were decreased. Furthermore, when conditioned medium from of 293 cells transfected with the fusion protein expression vector was added to the activated stellate cells, unlike the wild-type albumin, the fusion protein was found to be successfully incorporated into the stellate cells, induce the formation of fat droplets, and decrease the level of α-SMA. In addition, as the expression of mutated albumin with amino acid substitutions induces the senescence of stellate cells, the expression of mutant form of fusion protein also led to stellate cell senescence.

According to the present invention, the albumin used for the formation of fusion protein may be derived from any species, but may be preferably derived from humans, in order to avoid a risk of immunogenicity. Albumin may be encoded by a nucleic acid sequence as set forth in SEQ ID NO: 1, but the present invention is not limited thereto.

Since a high-affinity fatty acid binding site of albumin is present in an albumin I domain and an albumin III domain, it may be preferable to use the domains as a fusion partner, but the present invention is not limited thereto. Therefore, according to a specific example, the albumin used for the formation of fusion protein may be at least one of an albumin I domain and albumin III domain.

The albumin I domain may be encoded by a nucleic acid sequence (1st to 666th nucleic acids among the nucleic acids encoding albumin) as set forth in SEQ ID NO: 2, but the present invention is not limited thereto.

In addition, the albumin III domain may have a nucleic acid sequence (1216th to 1827th nucleic acids among the nucleic acids encoding albumin) as set forth in SEQ ID NO: 3, but the present invention is not limited thereto.

According to a specific example, in the case of locating the albumin III at a N-terminal side of the fusion protein, an albumin N-terminal including a secretory sequence may be added before the albumin III domain. The albumin N-terminal may be encoded by a nucleic acid sequence as set forth in SEQ ID NO: 4, but the present invention is not limited thereto.

Meanwhile, for the RBP bound to the albumin, the full sequence of the RBP or a part of the full sequence of the RBP may be used, and may be properly selected according to an albumin sequence to be bound or an order of binding with the albumin. The RBP may be encoded by a nucleic acid sequence (1st to 585th nucleic acids among the nucleic acid encoding the RBP) as set forth in SEQ ID NO: 5, a nucleic acid sequence (55th to 585th nucleic acids among the nucleic acid encoding the RBP) as set forth in SEQ ID NO: 6, or a nucleic acid sequence (55th to 603th nucleic acids among the nucleic acid encoding the RBP) as set forth in SEQ ID NO: 7, but the present invention is not limited thereto. For example, since when the RBP is bound to the C-terminal of the albumin, a secretory sequence may not be needed, the RBP peptide encoded by a nucleic acid as set forth in SEQ ID NO: 6 or SEQ ID NO: 7 may be used. In addition, in a case where an albumin domain is again bound to the C-terminal of the RBP, it may be preferable to use a partial peptide of the RBP encoded by a nucleic acid sequence as set forth in SEQ ID NO: 7 rather than the full sequence of the RBP.

According to a preferable specific example, the fusion protein may be albumin I domain-RBP-albumin III, albumin III-RBP-albumin I, RBP-albumin III, albumin III-RBP, an albumin-RBP, or RBP-albumin. The albumin I domain-RBP-albumin III is a type in which the N-terminal of the RBP is bound to the C-terminal of albumin I domain and the albumin III domain is bound to the C-terminal of the RBP. The RBP-albumin III, albumin III-RBP, albumin-RBP, and RBP-albumin are also interpreted in the same way. From the above-mentioned sequence analysis, the present inventors found that the fusion protein of the above-mentioned type does not inhibit a natural steric conformation of the albumin, and thus has no influence on a fatty acid binding site or on RBP binding through a RBP receptor. Therefore, the fusion protein may have any one amino acid sequence among amino acid sequences set forth in SEQ ID NO: 8 to SEQ ID NO: 13, but the present invention is not limited thereto. Specifically, the albumin I domain-RBP-albumin III, albumin III-RBP-albumin I, RBP-albumin III, albumin III-RBP, albumin-RBP, and RBP-albumin may have amino acid sequences set forth in SEQ ID NO: 8, SEQ ID NO: 9, SEQ ID NO: 10, SEQ ID NO: 11, SEQ ID NO: 12, and SEQ ID NO: 13, respectively. Those sequences may include an amino acid in the protein to be fused, an amino acid in the nucleic acid encoding a restriction site, a His tag for purifying, and the like.

According to another specific example, wild-type albumin, or the wild-type albumin having partially substituted amino acids, may be used to induce aging of stellate cells by the variation of albumin. According to a specific example, for the albumin or albumin III domain included in the fusion protein, Arg410, Tyr411, and Lys525 may be substituted with Ala, but the present invention is not limited thereto.

In addition, the present invention provides a polynucleotide encoding the above-mentioned fusion protein including the albumin and retinol-binding protein (RBP), a recombinant vector including the polynucleotide, and a transformant transformed by the recombinant vector.

According to the present invention, the polynucleotide may have nucleic acid sequences set forth in SEQ ID NO: 14 to SEQ ID NO: 19, but the present invention is not limited thereto. Specifically, albumin I domain-RBP-albumin III, albumin III-RBP-albumin I, RBP-albumin III, albumin III-RBP, albumin-RBP, and RBP-albumin may be respectively encoded by nucleic acid sequences set forth in SEQ ID NO: 14, SEQ ID NO: 15, SEQ ID NO: 16, SEQ ID NO: 17, SEQ ID NO: 18, and SEQ ID NO: 19, but the present invention is not limited thereto. Those sequences may include nucleic acids encoding the proteins to be fused, nucleic acids encoding restriction sites used for fusing proteins, a His tag for purifying, a stop codon, and the like.

According to another specific example, wild-type albumin, or the wild-type albumin having a partially substituted amino acid sequence among the amino acid sequences of the domain thereof may be used to induce aging of stellate cells by variation of the albumin. According to a specific example, for the albumin or albumin III domain included in the fusion protein, Arg410, Tyr411, and Lys525 may be substituted by Ala, but the present invention is not limited thereto.

Meanwhile, the recombinant vector including the polynucleotide may be prepared by inserting the polynucleotide into the known expression vector capable of being used for preparing a fusion protein. In the present invention, the term "vector" means a DNA construct including a DNA sequence operably bound to a proper regulatory sequence capable of expressing DNA in a proper host. A vector may be plasmid, phage particles, or simply a potential genome insert. In the case of transforming into a proper host, the vector can be replicated and can function regardless of a host genome, or may be integrated into the genome itself in some cases. Recently, plasmid is a type that is most generally used as a vector, so that in the present specification, "plasmid" and "vector" are used interchangeably. For purposes of the present invention, a plasmid vector is preferably used. A typical plasmid vector capable of being used for these purposes has (a) a replication origin that allows it to be effectively replicated to include hundreds of plasmid vectors per host cell, (b) antibiotic resistance genes allowing the host cell transformed into the plasmid vector to be selected, and (c) a structure including restriction enzyme cleavage sites capable of receiving insertion of an external DNA fragment. Even if there are no proper restriction enzyme cleavage sites, when a synthetic oligonucleotide adaptor or linker according to the general method is used, the vector and external DNA may be easily ligated.

Meanwhile, such a recombinant vector may include an expression vector allowing a His tag to be expressed at the end of a fusion protein in order to effectively isolate and purify a protein.

A host cell may be transformed by using a polynucleotide encoding a fusion protein including albumin and a retinol-binding protein (RBP) and a recombinant vector including the polynucleotide. The host cell used for expressing a fusion protein according to the present invention may include a cancer cell, but the present invention is not limited thereto.

In addition, the present invention provides a method of producing a fusion protein in which comprises albumin and a retinol-binding protein (RBP), comprising expressing the fusion protein in which comprises the albumin and the retinol-binding protein (RBP) from the transformant. The expression of the fusion protein from the transformant may be generally induced through culturing the host cell. The fusion protein comprising the albumin and retinol-binding protein (RBP) according to the present invention may be isolated from a culture medium by a known method for purifying a protein because the albumin and RBP themselves have a secretory signal, and thus the fusion protein is secreted out of the cell.

In the present invention, content in connection with genetic engineering technologies will be more clear by the content as disclosed in the document by Sambrook, et al. (Sambrook, et al. Molecular Cloning, A Laboratory Manual, Cold Spring Harbor laboratory Press, Cold Spring Harbor, N.Y. (2001)) and the document by Frederick, et al. (Frederick M. Ausubel et al., Current protocols in molecular biology volume 1, 2, 3, John Wiley & Sons, Inc. (1994)).

In addition, the present invention provides a pharmaceutical composition for preventing or treating fibrotic diseases, in which the composition comprises a fusion protein in which comprises albumin and a retinol-binding protein as an effective ingredient; a use of the fusion protein comprising the albumin and retinol-binding protein (RBP) for preparing a medicine for preventing or treating fibrotic diseases; and a method for preventing or treating fibrotic diseases, comprising administering to a subject the fusion protein comprising the albumin and retinol-binding protein (RBP) in a therapeutically effective dose.

According to a specific example, the fibrotic disease occurs in the liver, pancreas, lungs, kidneys, or intestines, but the present invention is not limited thereto. Examples of the fibrotic disease capable of being prevented or treated by the fusion protein according to the present invention include liver fibrosis, chronic hepatitis, cirrhosis, hepatic cancer, chemotherapy-associated steatohepatitis (CASH), lung fibrosis, renal fibrosis, renal failure, pancreatic fibrosis, chronic pancreatitis, and pancreatic cancer.

The pharmaceutical composition of the present invention may be preferably formulated into a pharmaceutical composition by further including at least one pharmaceutically acceptable carrier for administration in addition to an effective ingredient. Preferably, a liquid solution for an injection is suitable.

For the composition to be formulated in a liquid solution, the pharmaceutically acceptable carrier may include, to be suitable for sterilization and for a living body, saline solution, sterilized water, Ringer's solution, buffered saline, albumin injection solution, dextrose solution, maltodextrin solution, glycerol, ethanol. In combination with at least one of these components, and if necessary, other general additives, such as antioxidant, a buffer solution, and bacteristat may be added. In addition, a form of dose to be injected, such as an aqueous solution, suspension, and an emulsion, may be formulated by further adding diluents, dispersing agents, surfactants, binding agents, and a lubricant. Furthermore, it may be preferably formulated according to a disease or components by using the method disclosed in Remington's Pharmaceutical Science, Mack Publishing Company, Easton 5 PA, as a proper method in the art.

The pharmaceutical composition of the present invention may be administered in a general way through a route such as intravenous injection, intra-arterial injection, intraperitoneal injection, intramuscular injection, and intrasternal injection.

An effective dose of an effective ingredient of the pharmaceutical composition according to the present invention means the amount required for effectively preventing or treating diseases. Accordingly, the effective dose may be controlled according to various factors such as a type of disease, disease severity, types and contents of the effective ingredient and other ingredients of the composition, a form of administration, an age, body weight, general health conditions, sex and a diet of a patient, an administration time, an administration route, composition secretion rate, a treatment period, and drugs taken concurrently. For example, in the case of the adult, the fusion protein of the present invention may be administered in doses of 10 ng/kg to 10 g/kg when administrated once a day or several times a day, but the present invention is not limited thereto.

According to the present invention, subjects may be human, orangutan, chimpanzee, mouse, rat, dog, cow, chicken, pig, goat, and sheep, but they are preferably used.

Effects of the Invention

The fusion protein comprising albumin and retinol-binding protein (RBP) according to the present invention can be used for preventing or treating fibrotic diseases occurring in the liver, pancreas, lungs, or other organs by promoting formation of fat droplets in stellate cells and converting activated stellate cells into non-activated state or by inducing cellular senescence of the stellate cells.

DESCRIPTION OF DRAWINGS

FIG. 3 shows a cytomorphological effect of the expression of the mutant fusion protein including albumin/albumin III domains having induced point mutation (R410A/Y411A/K525A).

FIG. 8 shows the result of MT (Masson's trichrome) staining illustrating that the fusion protein according to the present invention reduces kidney fibrosis.

BEST MODE

Figure 1:
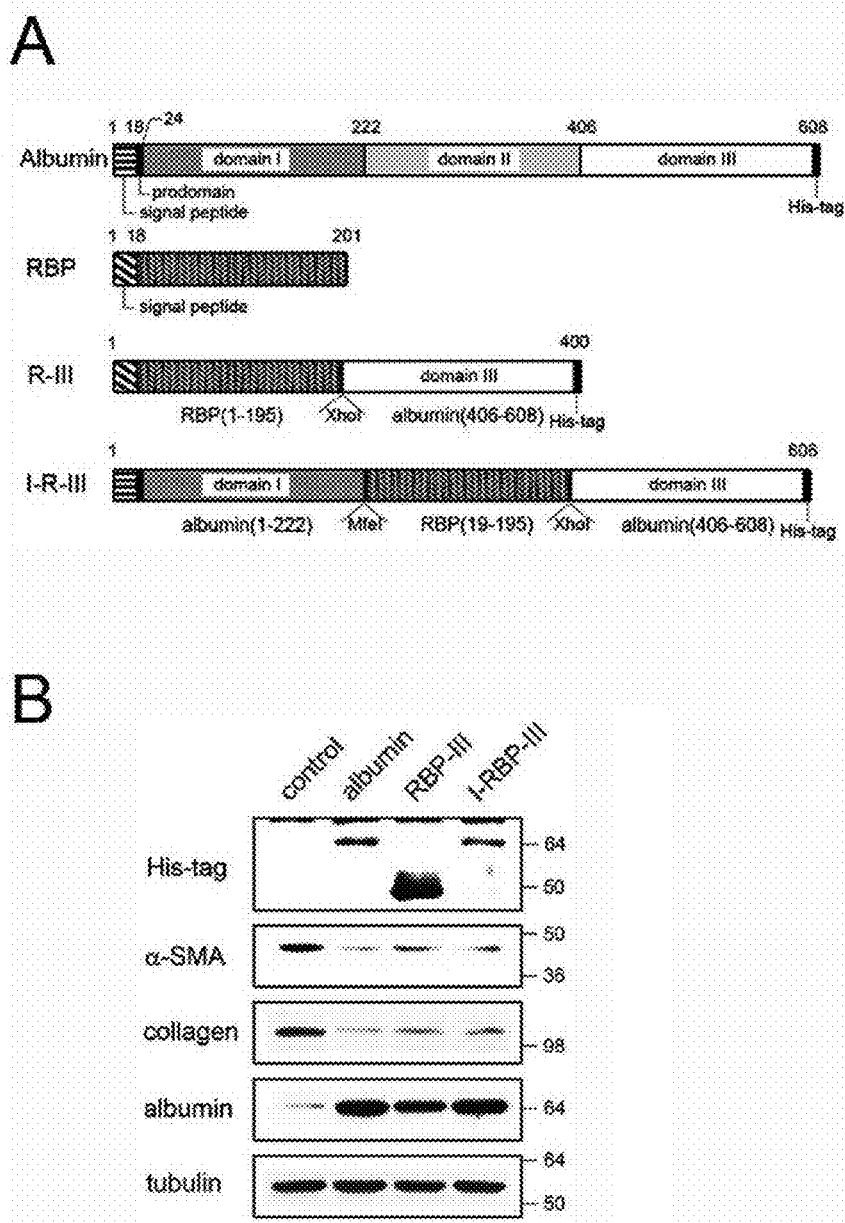
FIG. 1A is a schematic diagram illustrating production of the fusion protein of RBP-albumin$^{406-608 a.a. (domain\,III)}$ (R-III) and albumin$^{1-222\,(domain\,I)}$-RBP-albumin$^{406-608}$ (I-R-III)
FIG. 1B shows the result of western blot analysis assessing the effect of fusion protein expression on activated stellate cells.

The above and other objects, features and advantages of the present invention will become clear by describing Examples below in detail. However, the present invention is not limited to the Examples described below, and can be implemented in various different forms. The following Examples are provided so that this disclosure will completely enable those of ordinary skill in the art to embody and practice the present invention.

EXAMPLE

Experiment Method

Isolation and Culture of Pancreatic Stellate Cells (PSCs)

Rat pancreatic stellate cells were isolated according to the method disclosed in Apte, M. V. et al., Periacinar stellate shaped cells in rat pancreas: identification, isolation, and culture. Gut 43 (1), 128-133 (1998). In summary, pancreas was finely minced, placed in a Hank's buffer solution containing 0.05% collagenase, 0.02% protease, and 0.1% DNase, and then shaken at 37° C. for 20 minutes. After filtering through a 150 mm mesh, the cells were centrifuged by 13.2% Nycodenz gradient at 1400 g for 20 minutes. The pancreatic stellate cells were collected from the band just above the interface between the Nycodenz solution and aqueous layer, suspended in a DMEM (Dulbecco's modified Eagle's medium, Carlsbad, Calif.) supplemented with 10% fetal bovine serum, and then plated on a non-coated plastic dish. After reaching confluence in the primary culture, serial passages were obtained always applying 1:3 split.

Constitution of Expression Vector to Albumin-RBP Fusion Protein

Total RNA was extracted from a rat river tissue using a RNeasy kit (Qiagen, Valencia, Calif.) and reverse-transcribed into cDNA using GeneAmp RNA PCR (Applied Biosystems, Foster city, CA). The entire open reading frame (ORF) of albumin or RBP was amplified by polymerase chain reaction (PCR) with the designed primers and inserted into a pBluescript vector.

The expression vector encoding albumin I-RBP-albumin III (hereinafter, also referred to as 1R3 or I-RBP-III) was prepared as follows. A DNA fragment encoding albumin (domain I: 1-666) (SEQ ID NO: 2) or a RBP (55-585) (SEQ ID NO: 6) was amplified from the pBluescript-albumin or pBluescript-RBP by PCR with the primers:

```
                                         (SEQ ID NO: 2)
Albumin (domain I: 1-666)
Sense primer:
                                         (SEQ ID NO: 20)
5' GGGGTACCCC ACCATGAAGT GGGTAACCTT TC 3'

Antisense primer:
                                         (SEQ ID NO: 21)
5' CCCCAATTGC ATCCTCTGAC GGACAGC 3'

(SEQ ID NO: 6)
RBP (55-585)
Sense primer:
                                         (SEQ ID NO: 22)
5' GGGCAATTGG AGCGCGACTG CAGGGTG 3'

Antisense primer:
                                         (SEQ ID NO: 23)
5' CCCCTCGAGT CTGCTTTGAC AGTAACC 3'.
```

The PCR products were double digested with KpnI/MFeI or MfeI/XhoI, respectively, and the DNA fragments purified by an agarose gel electrophoresis were ligated together and then cloned into KpnI/XhoI-cut pBluescript vector to yield pBluescript-1R.

A DNA fragment encoding albumin (domain III: 1216-1827) (SEQ ID NO: 3) was amplified with the following primers:

```
Sense primer:
                                         (SEQ ID NO: 24)
5' GGGCTCGAGGAAGAACCTAAGAACTTG 3'

Antisense primer:
                                         (SEQ ID NO: 25)
5' GGCTCTAGAT TAATGATGAT GATGATGATGGGCTAAGGCT
TCTTTGCT 3'.
```

A His-tag sequence was included in the antisense primer. The PCR products were double digested with XhoI/XbaI and then ligated with the DNA fragment of IR prepared above.

The resulting DNA fragment 1R3 was inserted into expression vector pcDNA3.1+ at KpnI and XbaI sites to yield pcDNA3.1-1R3.

An expression vector encoding RBP-albumin III (hereinafter, also referred to as R3 or RBP-III) was prepared as follows. A DNA fragment encoding RBP (1-585) (SEQ ID NO: 5) was amplified with the following primers.

```
Sense primer:
                                         (SEQ ID NO: 26)
5' GCGGAATTCC ACCATGGAGT GGGTGTGGGC 3'

Antisense primer:
                                         (SEQ ID NO: 27)
5' CCCCTCGAGT CTGCTTTGAC AGTAACC 3'
```

The PCR products were double digested with EcoRI/XhoI, ligated with a DNA fragment encoding albumin (domain III: 1216-1827) (SEQ ID NO: 3), and then inserted into pcDNA3.1+ vector at EcoRI and XbaI sites to yield pcDNA3.1-R3. In the pcDNA3.1-1R3 or pcDNA3.1-R3, an albumin/RBP encoding region was located immediately upstream of 6-histidine tag encoding sequence and stop codon in the same reading frame.

Meanwhile, it has been reported that expression of mutant albumin, in which Arg410, Tyr411, and Lys525, amino acid residues of the albumin were substituted with Ala, leads to aging of stellate cells (Kim N, Yoo W, Lee J, Kim H, Lee H, Kim Y, Kim D, Oh J.* (2009) Formation of vitamin A fat droplets in pancreatic stellate cells requires albumin. Gut 58(10), 1382-90.). It means that direct interaction with fatty acids is an important mechanism for albumin function in stellate cells. Accordingly, in the present invention, a mutant fusion protein expression vector including albumin/albumin III domain having a point mutation (R410A/Y411A/K525A) induced, using a PCR-based method which was constructed using Muta-direct™ Site-Directed Mutagenesis Kit (iNtRON, Korea) in order to prepare a fusion protein for inducing aging of stellate cells; the expression vector was transfected into the activated stellate cells; and then a change of phenotype was investigated.

All the constructs were sequenced by using an auto-sequencer to confirm an albumin/RBP encoding region.

Purification of His6 Tag Recombinant Fusion Protein

An expression vector encoding mouse R3 was prepared in the same manner as the rat fusion protein. Primers used for a PCR were as follows.

```
                                         (SEQ ID NO: 3)
Albumin (domain III: 1216-1827)
Sense primer:
                                         (SEQ ID NO: 28)
5' GGGCTCGAGG AAGAGCCTAA GAACTTG 3'

Antisense primer:
                                         (SEQ ID NO: 29)
5' GGCTCTAGAT TAATGATGAT GATGATGATGGGCTAAGGTG
TCTTTGCA 3'

(SEQ ID NO: 5)
RBP (1-585)
Sense primer:
                                         (SEQ ID NO: 30)
5' GCGGAATTCC ACCATGGAGT GGGTGTGGGC 3'

Antisense primer:
                                         (SEQ ID NO: 31)
5' CCCCTCGAGC CTGCTTTGAC AGTAACC 3'
```

Clonal cell lines having high expression rate were selected by assessing a level of the secreted recombinant fusion protein by western blotting using an anti-His tag antibody after 293 cells were stably transfected with an expression vector encoding R3. A culture medium of 293 cells was fractionated with ammonium sulfate (55%), then subject to His Trap affinity column. The sample was further purified by a Resource Q. The purified proteins were dialyzed with deionized water, freeze-dried, and then dissolved in saline solution. As a result of measuring with a SDS-PAGE and protein staining, the purity of R-III was above 95%.

Transfection

Activated pancreas stellate cells (after passage 2) was transiently transfected using lipofectamine 2000 (Invitrogen, Carlsbad, Calif.), and then after 24 hours, the cells were analyzed.

Western Blotting Analysis

The cells were rinsed in ice-cold phosphate buffer saline (PBS) twice, and harvested by scraping in a lysis buffer solution. The equivalent amounts of proteins were separated by a SDS-PAGE, followed by immunoblot detection using a primary antibody. The primary antibodies were as follows: albumin (Santa Cruz, Santa Cruz, Calif.), α-SMA (Sigma, St. Louis, Mo.), α-tubulin (Cell signaling, Beverly, Mass.) and Type I collagen (Calbiochem, San Diego, Calif.), His-tag (AB Frontier, Seoul, Korea).

Immunofluorescence Analysis

Pancreatic stellate cells were plated on a glass cover slip coated with gelatin. The samples were fixed with paraformaldehyde, incubated with an albumin antibody (Santa Cruz #sc-58698) overnight at 4° C. in a moist chamber, and reacted with a secondary antibody bound with Alexa Fluor 568. The cells were washed with PBS and mounted onto a slide. The stained cells were visualized by using Zeiss AXIO Imager M1 microscope.

Oil Red O Staining

Fat droplets were visualized by staining the pancreatic stellate cells with an oil red O using the method disclosed by Koopman (Koopman, R., Schaart, G., & Hesselink, M. K., Optimisation of oil red O staining permits combination with immunofluorescence and automated quantification of lipids. Histochem Cell Biol 116 (1), 63-68 (2001)). The oil red O was diluted in triethyl phosphate instead of isopropane.

Preparation of Liver Fibrosis Model

BALB/c mice were injected intraperitoneally with 1 mL/kg $CCl_4$ dissolved in a mineral oil at 1:1 three times per week for 7 weeks to induce liver damage and prepare liver fibrosis mouse model having damaged liver. The group administered only mineral oil in the same amount thereof was used as a control group. At 72 hours after final CCl4 injection, the mouse was sacrificed. The hepatic tissue was sectioned and fixed with 10% buffer formalin in order for histological analysis. The remnant was added to a Rnase-free tube and quickly frozen in liquid nitrogen.

Preparation of Kidney Fibrosis Model

UUO (unilateral ureteral obstruction) model was performed by using a BALB/c mouse. In summary, the abdominal cavity of the mouse was opened through a midline incision, and then the left ureter was isolated and tied up. By a similar method, sham-operated animals were subjected to the same surgical operation, but the ureter ligation was not performed. In order to test an effect of albumin-RBP fusion protein R-III on improving kidney fibrosis, the R-III was administrated every day for 7 days through the tail vein injection from starting on the sixth day after blocking. After completing the test, the mouse was sacrificed, and then the kidney tissues were removed. The half of the kidney was fixed with 10% buffer formalin in order for a histological study, and the other half was snap-frozen in liquid nitrogen to store at −80° C. in order for extractions of protein and RNA.

Immunohistological Analysis

The section (5 μm thickness) of formalin-fixed, paraffin-embedded liver tissues were prepared, stained with a H&E for a histological analysis and with Sirius red or Masson's trichrome for collagen deposition. In addition, the tissue sections were immunohistochemically stained with Type I collagen (Abcam, Cambridge, UK) antibody. In order to quantify the Sirius red staining, Image J software (NIH) was used.

Statistical Analysis

The results were expressed as mean±standard deviation (SD). A statistical analysis was performed by using t-tests. Comparisons were considered significant at $P<0.05$, and the P values were two-tailed.

Experimental Result

Facilitation of Formation of Fat Droplets in Pancreatic Stellate Cells of Albumin-RBP Fusion Protein In the aforementioned RBP-albumin$^{406-608\ a.a.\ (domain\ III)}$ (R-III) and albumin$^{1-222\ (domain\ I)}$-RBP-albumin$^{406-608}$ (I-R-III) (FIG. 1A), the respective protein parts were linked through restriction enzyme recognition site linkers and a polyhistidine tag was located at the C-terminal of fusion protein. After the pancreatic stellate cells were activated by serial passages (two passages), the cells were transfected with an expression vector to wild-type albumin, R-III or I-R-III and then a change of phenotype was investigated. As a result of western blotting, the fusion protein having the expected size was expressed (R-III ~45 kDa and I-R-III ~68 kDa (FIG. 1B)).

Figure 2:
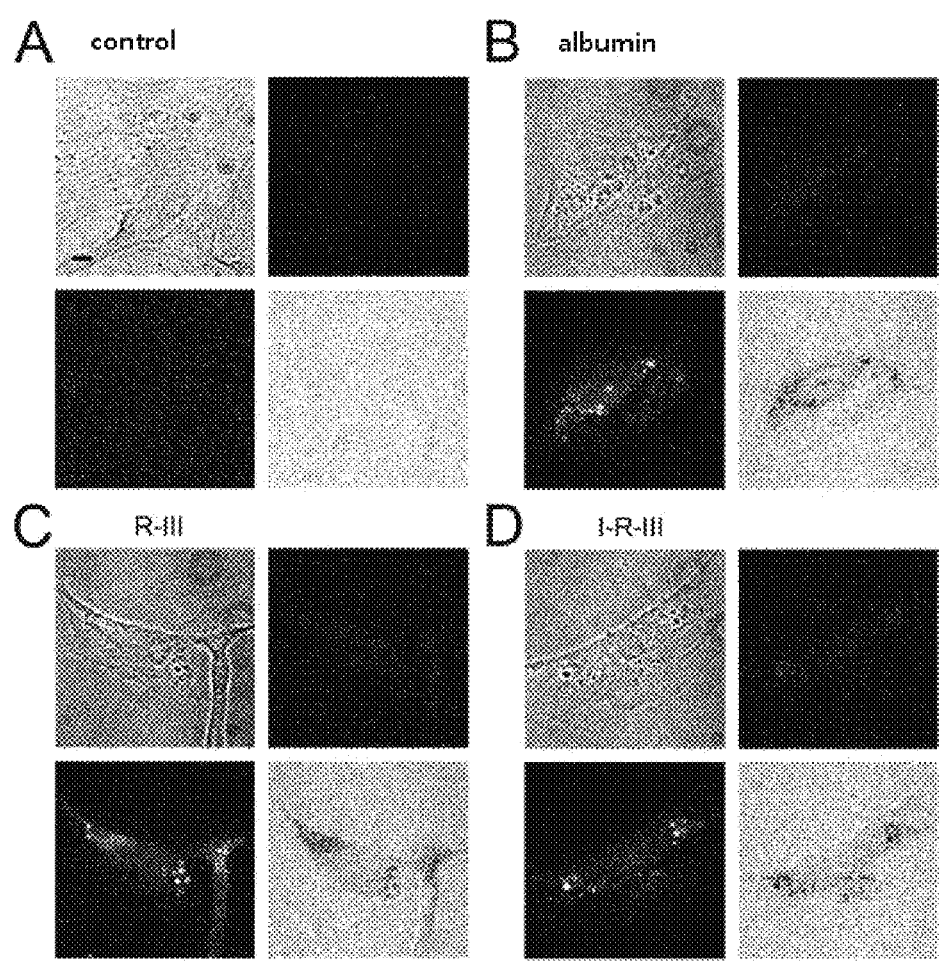
FIGS. 2A to 2D show the effect of the expression of albumin or fusion protein on cell morphology of activated stellate cells; phase contrast image (the left top panel), autofluorescence image (the right top panel), immunofluorescence (the right bottom panel), and oil red O staining (the left bottom panel).

FIGS. 2A to 2D show the results of analyzing a cell morphological effect of the albumin or fusion protein expression on the activated stellate cells; phase contrast image (left top panel), autofluorescens image (right top panel), immunofluorescence (Right bottom panel), and oil red O staining (left bottom panel). Activated pancreatic stellate cells under normal culture conditions show a shape of fibroblastoid (FIG. 2A), but expression of wild-type albumin, R-III or I-R-III induced formation of autofluorescent fat droplets, resulting in changing a cell shape into a polygonal shape (FIGS. 2B to 2D). Such a change of cell shape is accompanied with a decrease in levels α-SMA, a marker for the activated stellate cells, and type I collagen (FIG. 1B). This supports that, like albumin, expression of the fusion protein can inactivate the activated stellate cells.

Meanwhile, as a result of experimenting with a mutant fusion protein including the albumin/albumin III domain having an induced point mutation (R410A/Y411A/K525A) performed by the above-mentioned method, the expression of the mutant fusion protein led to a slight increase in lipid droplet formation and cellular senescence (FIG. 3).

Cellular Uptake of Albumin-RBP Fusion Protein into Stellate Cells

Figure 4:
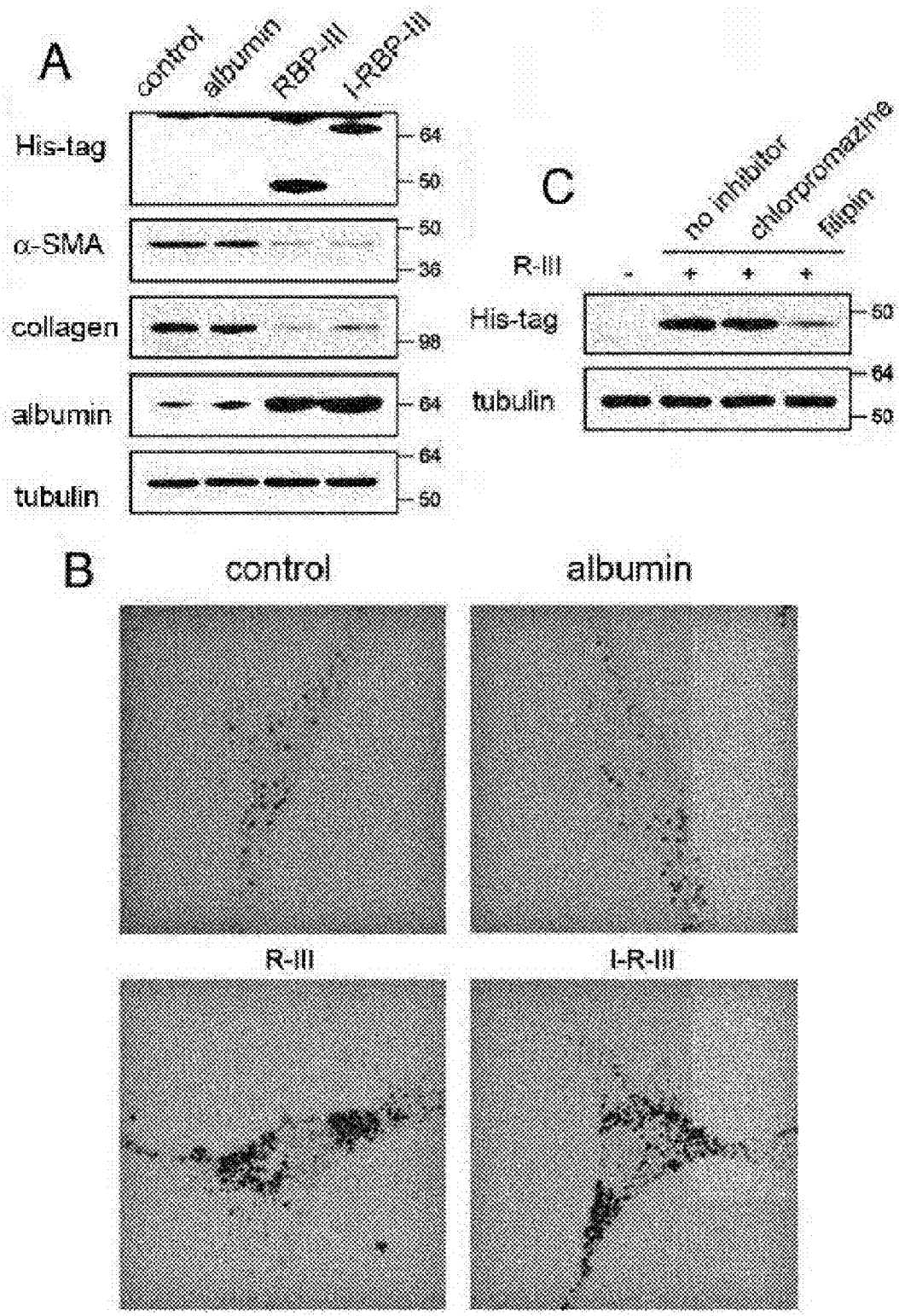
FIG. 4A shows the result of western blot analysis illustrating that the fusion protein according to the present invention is taken into stellate cells and induces biochemical changes.
FIG. 4B shows the result of an oil red O staining, describing morphological changes of cell type due to introduction of the fusion protein.
FIG. 4C shows the result of western blott analysis indicating that the fusion protein uptake is mediated through caveolae-mediated endocytosis.

In order to investigate whether the RBP moiety can facilitate cellular uptake of the fusion protein, conditioned medium was prepared by incubating the 293 cells stably transfected with albumin, R-III, or I-R-III for 24 hours, and applied to activated pancreatic stellate cells. Western blotting with use of anti-His tag antibody revealed that fusion proteins, but not wild-type albumin, were successfully incorporated into stellate cells (FIG. 4A). In addition, fusion proteins induced phenotypic conversion (FIG. 4B), and reduced the expression levels of α-SMA and Type I collagen (FIG. 4A). We further investigated a mechanism of R-III internalization using an inhibitor of clathrin-mediated endocytosis (chlorpromazine)

and an inhibitor of caveolae-mediated endocytosis (filipin). Western blotting analysis revealed that cellular uptake of R-III was largely inhibited by filipin pre-treatment (FIG. 4C). This result agrees with the previous report that RBP enters the cell through caveolae-mediated endocytosis. Therefore, the data shows that the constituent parts of the fusion protein are functionally important. In other words, in the fusion protein, the RBP performs a role in stellate cells-specific targeting moiety and albumin domain performs a role in stellate cells inactivating domain.

Absorption of Injected Albumin-RBP Fusion Protein into Liver

Figure 5:
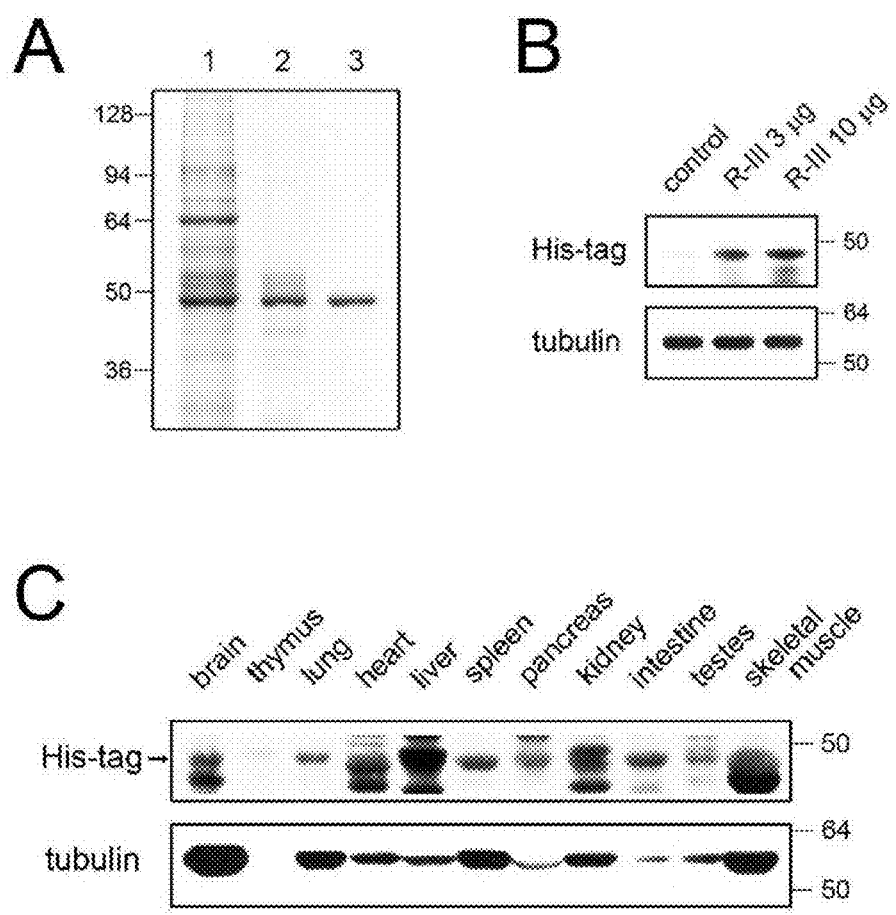
FIG. 5A shows the purification process for the albumin-RBP fusion protein according to the present invention using an ammonium sulfate precipitation (lane 1), a His Trap affinity column (lane 2), and a Resource Q column (lane 3)
FIG. 5B shows the result of western blot analysis of hepatic tissue lysate after an intravenous injection of the fusion protein for 1 week.
FIG. 5C shows the result of in vivo experiment illustrating tissue distribution.

Since then, tissue distribution of albumin-RBP fusion protein was investigated in vivo. Since R-III was expressed and secreted more (data not shown) from the transfected 293 cells as compared with I-R-III, R-III was selected and purified using FPLC to >95% purity (FIG. 5A). The R-III (3 or 10 µg) dissolved in 0.1 ml of saline solution was injected every day into the tail vein of a BALB/c mouse for 7 days, and then liver lysate was analyzed by western blotting using an anti-His tag antibody. The distinct R-III protein band was observed in the R-III-injected mouse, and the band intensity thereof increased in dose dependent manner (FIG. 5B). When equivalent amounts of whole cell lysates obtained from different tissues was analyzed by western blotting, strong R-III signal was observed in liver, and also a weak signal was detected in the brain, lungs, spleen, pancreas, kidneys, and intestines (FIG. 5C). Such tissue distribution of R-III appears to be similar to that of RBP.

Improvement of Liver Fibrosis by R-III

Figure 6:
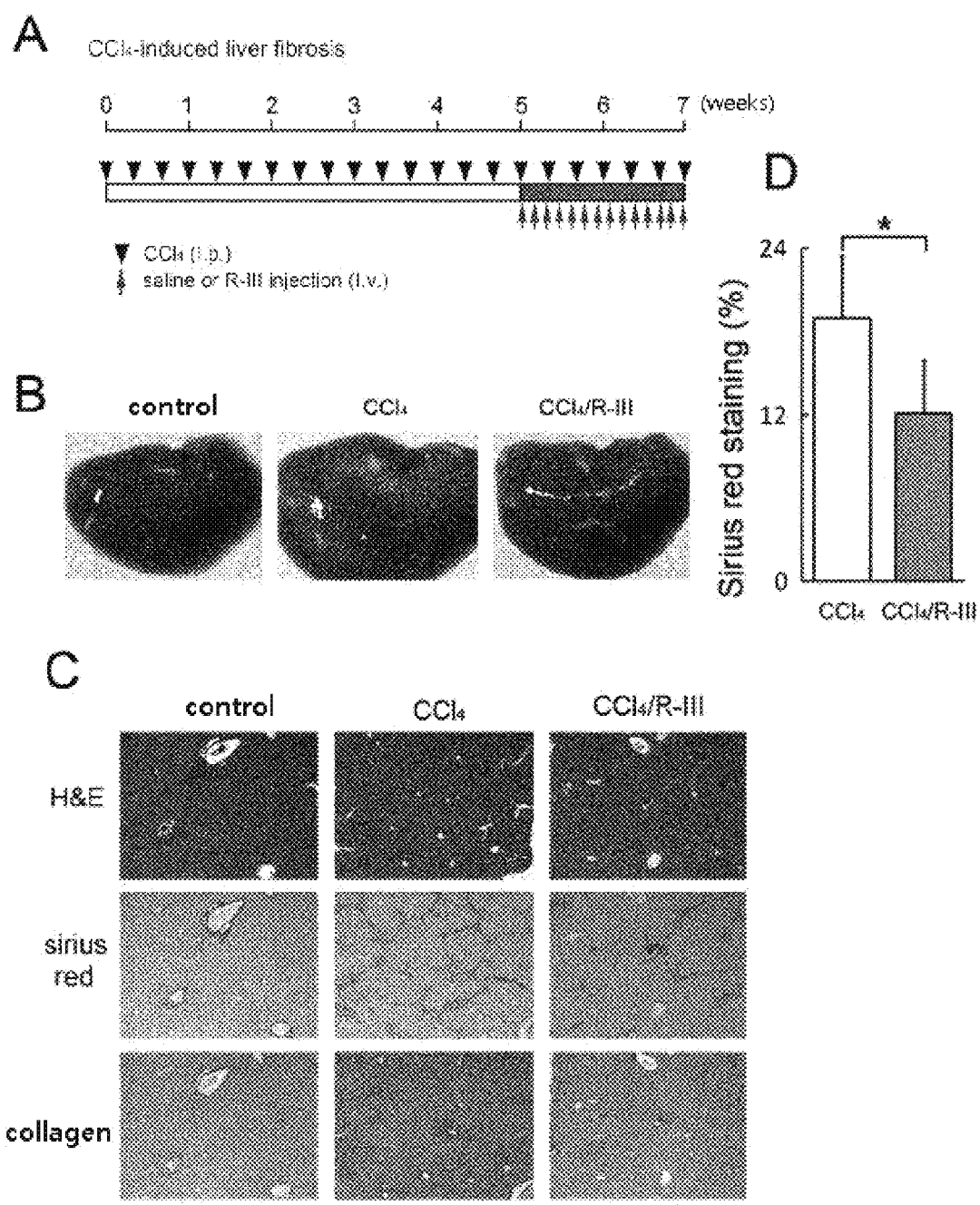
FIG. 6 shows the results of immunohistochemical analysis and Sirius red staining, and a photomicrograph illustrating that the fusion protein according to the present invention alleviates liver fibrosis.

The present inventors assessed therapeutic and preventive potentials of R-III using the carbon tetrachloride ($CCl_4$)-induced liver fibrosis model. $CCl_4$ was injected three time per week into the abdominal cavity of a BALB/c mouse for 7 weeks, and then R-III (10 µg; n=25), albumin (10 µg; n=7), RBP (5 µg; n=5), or saline solution alone (n=23) was intravenously administered every day during the last 2 weeks in the $CCl_4$ treatment (FIG. 6A). The mineral oil/saline solution control mice exhibited a normal liver structure (FIG. 6C). Meanwhile, severe liver fibrosis was observed in $CCl_4$-treated mice. In other words, multiple nodules were found on the surface of the liver under a microscope (FIG. 6B), and destruction of the liver tissue architecture, fibrous expansion, and large fibrous septa formation were observed (FIG. 6C). In addition, the Sirius red staining and immunohistochemical analysis exhibited extensive collagen deposition in the liver tissue of $CCl_4$-treated mice (FIG. 6C). However, the administration of R-III significantly reduced nodule incidence, histopathological alterations and collagen deposition, which were shown in the $CCl_4$-treated group (FIGS. 6B and 6C). Quantification of Sirius red staining by Image J Software (NIH) showed that collagen content was decreased by R-III by ~35% (FIG. 6D). On the other hand, the administration of albumin or RBP did not influence progress of fibrosis by treating CCl4 (data not shown). As a result, it was identified that the administration of R-III was a remedy for liver fibrosis for the $CCl_4$-induced liver fibrosis mouse model.

Effect of R-III on Inhibiting Liver Fibrosis

Figure 7:
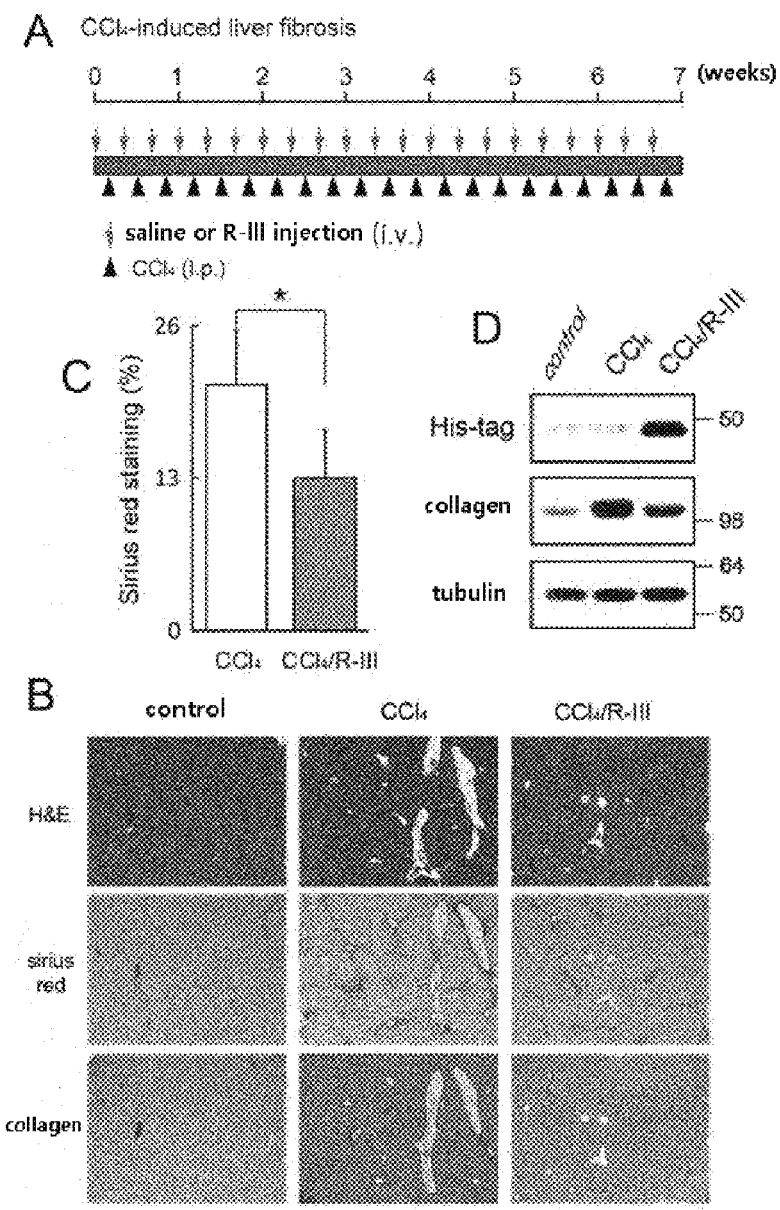
FIG. 7 shows the results of Sirius red staining, immunohistochemical staining and western blotting, illustrating that the fusion protein according to the present invention prevents liver fibrosis.

To examine whether R-III might have preventive effect on $CCl_4$-induced liver fibrosis, mice (n=22) were treated with $CCl_4$ and R-III (10 µg) three times per week over 7 weeks. The CCl4 and R-III were administrated on different days (FIG. 7A). H&E and Sirius red staining of liver sections revealed that R-III markedly reduced histopathological alterations and collagen deposition (FIG. 7B). As a result of quantitative analysis of Sirius red staining, it was confirmed that a content of collagen was decreased by ~38% (FIG. 7C). This result was further supported by immunohistochemical staining and western blotting (FIGS. 7B and 7D). Therefore, the present inventors' data showed that the albumin-RBP fusion protein has both a therapeutic and preventive effects on liver fibrosis.

Kidney Fibrosis Decrease by R-III

The therapeutic potential of R-III was estimated using a UUO (unilateral ureteral obstruction)-induced kidney fibrosis model. The mice were subjected to UUO and then intravenously administered R-III (10 µg; n=10) or saline solution (n=10) every day for 7 days (FIG. 8A). MT (Masson's trichrome) staining of kidney sections confirmed extensive collagen deposition in UUO-mediated fibrotic kidney and R-III markedly reduced collagen deposition (FIG. 8B). Therefore, from this result, it was confirmed that the RAH attenuated UUO-induced kidney fibrosis in the mouse.

The invention claimed is:

1. A fusion protein comprising albumin and a retinol-binding protein (RBP), wherein the fusion protein has any one of the amino acid sequences set forth in SEQ ID NOs: 8 to 13.

2. The fusion protein of claim 1, wherein the albumin is at least one of an albumin I domain and an albumin III domain.

3. The fusion protein of claim 1, wherein the fusion protein is albumin I domain-RBP-albumin III, albumin III-RBP-albumin I, RBP-albumin III, albumin III-RBP, albumin-RBP, or RBP-albumin.

4. A polynucleotide encoding the fusion protein of claim 1.

5. The polynucleotide of claim 4, wherein the polynucleotide has any one of nucleic acid sequences set forth in SEQ ID NO: 14 to SEQ ID NO: 19.

6. A fusion protein comprising albumin and a retinol-binding protein (RBP), wherein the fusion protein comprises the amino acid sequence selected from the croup consisting of SEQ ID NO 8, SEQ ID NO 9, SEQ ID NO 10, SEQ ID NO 11, SEQ ID NO 12, and SEQ ID NO 13.

7. The fusion protein of claim 6, wherein the albumin is at least one of an albumin I domain and an albumin III domain.

8. The fusion protein of claim 6, wherein the fusion protein comprises the amino acid sequence set forth in SEQ ID NO: 8.

9. The fusion protein of claim 6, wherein the fusion protein comprises the amino acid sequence set forth in SEQ ID NO: 9.

10. The fusion protein of claim 6, wherein the fusion protein comprises the amino acid sequence set forth in SEQ ID NO: 10.

11. The fusion protein of claim 6, wherein the fusion protein comprises the amino acid sequence set forth in SEQ ID NO: 11.

12. The fusion protein of claim 6, wherein the fusion protein comprises the amino acid sequence set forth in SEQ ID NO: 12.

13. The fusion protein of claim 6, wherein the fusion protein comprises the amino acid sequence set forth in SEQ ID NO: 13.

* * * * *

SEQUENCE LISTING

<160> NUMBER OF SEQ ID NOS: 35

<210> SEQ ID NO 1
<211> LENGTH: 1827
<212> TYPE: DNA
<213> ORGANISM: Homo sapiens

<400> SEQUENCE: 1

```
atgaagtggg taacctttat ttcccttctt tttctcttta gctcggctta ttccaggggt      60
gtgtttcgtc gagatgcaca caagagtgag gttgctcatc ggtttaaaga tttgggagaa     120
gaaaatttca aagccttggt gttgattgcc tttgctcagt atcttcagca gtgtccatt      180 gaagatcatg taaaattagt gaatgaagta actgaatttg caaaaacatg tgttgctgat     240
gagtcagctg aaaattgtga caaatcactt catacccttt ttggagacaa attatgcaca     300
gttgcaactc ttcgtgaaac ctatggtgaa atggctgact gctgtgcaaa acaagaacct     360
gagagaaatg aatgcttctt gcaacacaaa gatgacaacc caaacctccc ccgattggtg     420
agaccagagg ttgatgtgat gtgcactgct tttcatgaca atgaagagac atttttgaaa     480
aaatacttat atgaaattgc cagaagacat ccttactttt atgccccgga actccttttc     540
```

```
tttgctaaaa ggtataaagc tgcttttaca gaatgttgcc aagctgctga taaagctgcc        600
tgcctgttgc caaagctcga tgaacttcgg gatgaaggga aggcttcgtc tgccaaacag        660
agactcaagt gtgccagtct ccaaaaattt ggagaaagag ctttcaaagc atgggcagta        720
gctcgcctga gccagagatt tcccaaagct gagtttgcag aagtttccaa gttagtgaca        780
gatcttacca agtccacac ggaatgctgc catggagatc tgcttgaatg tgctgatgac         840
agggcggacc ttgccaagta tatctgtgaa atcaagatt cgatctccag taaactgaag         900
gaatgctgtg aaaaacctct gttggaaaaa tcccactgca ttgccgaagt ggaaaatgat        960
gagatgcctg ctgacttgcc ttcattagct gctgattttg ttgaaagtaa ggatgtttgc       1020
aaaaactatg ctgaggcaaa ggatgtcttc ctgggcatgt ttttgtatga atatgcaaga       1080
aggcatcctg attactctgt cgtgctgctg ctgagacttg ccaagacata tgaaaccact       1140
ctagagaagt gctgtgccgc tgcagatcct catgaatgct atgccaaagt gttcgatgaa       1200
tttaaacctc ttgtggaaga gcctcagaat ttaatcaaac aaaattgtga gcttttttgag      1260 cagcttggag agtacaaatt ccagaatgcg ctattagttc gttacaccaa gaaagtaccc       1320
caagtgtcaa ctccaactct tgtagaggtc tcaagaaacc taggaaaagt gggcagcaaa       1380
tgttgtaaac atcctgaagc aaaaagaatg ccctgtgcag aagactatct atccgtggtc       1440
ctgaaccagt tatgtgtgtt gcatgagaaa acgccagtaa gtgacagagt caccaaaatgc     1500 tgcacagaat ccttggtgaa caggcgacca tgcttttcag ctctggaagt cgatgaaaca       1560
tacgttccca aagagtttaa tgctgaaaca ttcaccttcc atgcagatat atgcacactt       1620
tctgagaagg agagacaaat caagaaacaa actgcacttg ttgagctcgt gaaacacaag       1680
cccaaggcaa caaagagca actgaaagct gttatggatg atttcgcagc ttttgtagag       1740
aagtgctgca aggctgacga taaggagacc tgctttgccg aggagggtaa aaaacttgtt       1800
gctgcaagtc aagctgcctt aggctta                                          1827
```

<210> SEQ ID NO 2
<211> LENGTH: 666
<212> TYPE: DNA
<213> ORGANISM: Homo sapiens

<400> SEQUENCE: 2

```
atgaagtggg taacctttat ttcccttctt tttctctttta gctcggctta ttccaggggt        60
gtgtttcgtc gagatgcaca caagagtgag gttgctcatc ggtttaaaga tttgggagaa       120
gaaaatttca agccttggt gttgattgcc tttgctcagt atcttcagca gtgtccattt        180
gaagatcatg taaaattagt gaatgaagta actgaatttg caaaaacatg tgttgctgat       240
gagtcagctg aaaattgtga caaatcactt catacccttt ttggagacaa attatgcaca       300
gttgcaactc ttcgtgaaac ctatggtgaa atggctgact gctgtgcaaa acaagaacct       360
gagagaaatg aatgcttctt gcaacacaaa gatgacaacc caaacctccc ccgattggtg       420
agaccagagg ttgatgtgat gtgcactgct tttcatgaca atgaagagac atttttgaaa       480
aaatacttat atgaaattgc cagaagacat ccttactttt atgccccgga actccttttc       540
tttgctaaaa ggtataaagc tgcttttaca gaatgttgcc aagctgctga taaagctgcc       600
tgcctgttgc caaagctcga tgaacttcgg gatgaaggga aggcttcgtc tgccaaacag       660
agactc                                                                 666
```

<210> SEQ ID NO 3

<211> LENGTH: 612
<212> TYPE: DNA
<213> ORGANISM: Homo sapiens

<400> SEQUENCE: 3

```
gaagagcctc agaatttaat caaacaaaat tgtgagcttt ttgagcagct tggagagtac    60
aaattccaga atgcgctatt agttcgttac accaagaaag taccccaagt gtcaactcca   120
actcttgtag aggtctcaag aaacctagga aaagtgggca gcaaatgttg taaacatcct   180
gaagcaaaaa gaatgccctg tgcagaagac tatctatccg tggtcctgaa ccagttatgt   240
gtgttgcatg agaaaacgcc agtaagtgac agagtcacca atgctgcac agaatccttg    300
gtgaacaggc gaccatgctt ttcagctctg gaagtcgatg aaacatacgt tcccaaagag   360
tttaatgctg aaacattcac cttccatgca gatatatgca cactttctga aggagagaga  420
caaatcaaga acaaactgc acttgttgag ctcgtgaaac acaagcccaa ggcaacaaaa    480
gagcaactga agctgttat ggatgatttc gcagcttttg tagagaagtg ctgcaaggct    540
gacgataagg agacctgctt tgccgaggag ggtaaaaaac ttgttgctgc aagtcaagct   600
gccttaggct ta                                                       612
```

<210> SEQ ID NO 4
<211> LENGTH: 84
<212> TYPE: DNA
<213> ORGANISM: Homo sapiens

<400> SEQUENCE: 4

```
atgaagtggg taacctttat ttcccttctt tttctcttta gctcggctta ttccaggggt    60
gtgtttcgtc gagatgcaca caag                                          84
```

<210> SEQ ID NO 5
<211> LENGTH: 585
<212> TYPE: DNA
<213> ORGANISM: Homo sapiens

<400> SEQUENCE: 5

```
atgaagtggg tgtgggcgct cttgctgttg gcggcgctgg gcagcggccg cgcggagcgc    60
gactgccgag tgagcagctt ccgagtcaag gagaacttcg acaaggctcg cttctctggg   120
acctggtacg ccatggccaa gaaggacccc gagggcctct ttctgcagga caacatcgtc   180
gcggagttct ccgtggacga gaccggccag atgagcgcca cagccaaggg ccgagtccgt   240
cttttgaata ctgggacgt gtgcgcagac atggtgggca ccttcacaga caccgaggac   300
cctgccaagt tcaagatgaa gtactggggc gtagcctcct ttctccagaa aggaaatgat   360
gaccactgga tcgtcgacac agactacgac acgtatgccg tgcagtactc ctgccgcctc   420
ctgaacctcg atggcacctg tgctgacagc tactccttcg tgttttcccg ggaccccaac   480
ggcctgcccc cagaagcgca gaagattgta aggcagcggc aggaggagct gtgcctggcc   540
aggcagtaca ggctgatcgt ccacaacggt tactgcgatg cagaa                   585
```

<210> SEQ ID NO 6
<211> LENGTH: 531
<212> TYPE: DNA
<213> ORGANISM: Homo sapiens

<400> SEQUENCE: 6

```
gagcgcgact gccgagtgag cagcttccga gtcaaggaga acttcgacaa ggctcgcttc    60
tctgggacct ggtacgccat ggccaagaag gaccccgagg gcctctttct gcaggacaac   120
```

| | |
|---|---|
| atcgtcgcgg agttctccgt ggacgagacc ggccagatga gcgccacagc caagggccga | 180 |
| gtccgtcttt tgaataactg gacgtgtgc gcagacatgg tgggcacctt cacagacacc | 240 |
| gaggaccctg ccaagttcaa gatgaagtac tggggcgtag cctcctttct ccagaaagga | 300 |
| aatgatgacc actggatcgt cgacacagac tacgacacgt atgccgtgca gtactcctgc | 360 |
| cgcctcctga acctcgatgg cacctgtgct gacagctact ccttcgtgtt ttcccgggac | 420 |
| cccaacggcc tgcccccaga agcgcagaag attgtaaggc agcggcagga ggagctgtgc | 480 |
| ctggccaggc agtacaggct gatcgtccac aacggttact gcgatggcag a | 531 |

<210> SEQ ID NO 7
<211> LENGTH: 549
<212> TYPE: DNA
<213> ORGANISM: Homo sapiens

<400> SEQUENCE: 7

| | |
|---|---|
| gagcgcgact gccgagtgag cagcttccga gtcaaggaga acttcgacaa ggctcgcttc | 60 |
| tctgggacct ggtacgccat ggccaagaag gaccccgagg gcctctttct gcaggacaac | 120 |
| atcgtcgcgg agttctccgt ggacgagacc ggccagatga gcgccacagc caagggccga | 180 |
| gtccgtcttt tgaataactg gacgtgtgc gcagacatgg tgggcacctt cacagacacc | 240 |
| gaggaccctg ccaagttcaa gatgaagtac tggggcgtag cctcctttct ccagaaagga | 300 |
| aatgatgacc actggatcgt cgacacagac tacgacacgt atgccgtgca gtactcctgc | 360 |
| cgcctcctga acctcgatgg cacctgtgct gacagctact ccttcgtgtt ttcccgggac | 420 |
| cccaacggcc tgcccccaga agcgcagaag attgtaaggc agcggcagga ggagctgtgc | 480 |
| ctggccaggc agtacaggct gatcgtccac aacggttact gcgatggcag atcagaaaga | 540 |
| aaccttttg | 549 |

<210> SEQ ID NO 8
<211> LENGTH: 613
<212> TYPE: PRT
<213> ORGANISM: Homo sapiens

<400> SEQUENCE: 8

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
                20                  25                  30

His Arg Phe Lys Asp Leu Gly Glu Glu Asn Phe Lys Ala Leu Val Leu
            35                  40                  45

Ile Ala Phe Ala Gln Tyr Leu Gln Gln Cys Pro Phe Glu Asp His Val
        50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys

```
145                 150                 155                 160
Lys Tyr Leu Tyr Glu Ile Ala Arg Arg His Pro Tyr Phe Tyr Ala Pro
                165                 170                 175
Glu Leu Leu Phe Phe Ala Lys Arg Tyr Lys Ala Ala Phe Thr Glu Cys
                180                 185                 190
Cys Gln Ala Ala Asp Lys Ala Ala Cys Leu Leu Pro Lys Leu Asp Glu
                195                 200                 205
Leu Arg Asp Glu Gly Lys Ala Ser Ser Ala Lys Gln Arg Leu Gln Leu
        210                 215                 220
Glu Arg Asp Cys Arg Val Ser Ser Phe Arg Val Lys Glu Asn Phe Asp
225                 230                 235                 240
Lys Ala Arg Phe Ser Gly Thr Trp Tyr Ala Met Ala Lys Lys Asp Pro
                245                 250                 255
Glu Gly Leu Phe Leu Gln Asp Asn Ile Val Ala Glu Phe Ser Val Asp
                260                 265                 270
Glu Thr Gly Gln Met Ser Ala Thr Ala Lys Gly Arg Val Arg Leu Leu
                275                 280                 285
Asn Asn Trp Asp Val Cys Ala Asp Met Val Gly Thr Phe Thr Asp Thr
        290                 295                 300
Glu Asp Pro Ala Lys Phe Lys Met Lys Tyr Trp Gly Val Ala Ser Phe
305                 310                 315                 320
Leu Gln Lys Gly Asn Asp Asp His Trp Ile Val Asp Thr Asp Tyr Asp
                325                 330                 335
Thr Tyr Ala Val Gln Tyr Ser Cys Arg Leu Leu Asn Leu Asp Gly Thr
                340                 345                 350
Cys Ala Asp Ser Tyr Ser Phe Val Phe Ser Arg Asp Pro Asn Gly Leu
        355                 360                 365
Pro Pro Glu Ala Gln Lys Ile Val Arg Gln Arg Gln Glu Glu Leu Cys
370                 375                 380
Leu Ala Arg Gln Tyr Arg Leu Ile Val His Asn Gly Tyr Cys Asp Gly
385                 390                 395                 400
Arg Leu Glu Glu Glu Pro Gln Asn Leu Ile Lys Gln Asn Cys Glu Leu
                405                 410                 415
Phe Glu Gln Leu Gly Glu Tyr Lys Phe Gln Asn Ala Leu Leu Val Arg
                420                 425                 430
Tyr Thr Lys Lys Val Pro Gln Val Ser Thr Pro Thr Leu Val Glu Val
            435                 440                 445
Ser Arg Asn Leu Gly Lys Val Gly Ser Lys Cys Cys Lys His Pro Glu
        450                 455                 460
Ala Lys Arg Met Pro Cys Ala Glu Asp Tyr Leu Ser Val Val Leu Asn
465                 470                 475                 480
Gln Leu Cys Val Leu His Glu Lys Thr Pro Val Ser Asp Arg Val Thr
                485                 490                 495
Lys Cys Cys Thr Glu Ser Leu Val Asn Arg Arg Pro Cys Phe Ser Ala
                500                 505                 510
Leu Glu Val Asp Glu Thr Tyr Val Pro Lys Glu Phe Asn Ala Glu Thr
            515                 520                 525
Phe Thr Phe His Ala Asp Ile Cys Thr Leu Ser Glu Lys Glu Arg Gln
            530                 535                 540
Ile Lys Lys Gln Thr Ala Leu Val Glu Leu Val Lys His Lys Pro Lys
545                 550                 555                 560
Ala Thr Lys Glu Gln Leu Lys Ala Val Met Asp Asp Phe Ala Ala Phe
                565                 570                 575
```

```
Val Glu Lys Cys Cys Lys Ala Asp Asp Lys Glu Thr Cys Phe Ala Glu
            580                 585                 590

Glu Gly Lys Lys Leu Val Ala Ala Ser Gln Ala Ala Leu Gly Leu His
        595                 600                 605

His His His His His
        610

<210> SEQ ID NO 9
<211> LENGTH: 619
<212> TYPE: PRT
<213> ORGANISM: Homo sapiens

<400> SEQUENCE: 9

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Gln Leu Glu Glu
            20                  25                  30

Pro Gln Asn Leu Ile Lys Gln Asn Cys Glu Leu Phe Glu Gln Leu Gly
        35                  40                  45

Glu Tyr Lys Phe Gln Asn Ala Leu Leu Val Arg Tyr Thr Lys Lys Val
50                  55                  60

Pro Gln Val Ser Thr Pro Thr Leu Val Glu Val Ser Arg Asn Leu Gly
65                  70                  75                  80

Lys Val Gly Ser Lys Cys Cys Lys His Pro Glu Ala Lys Arg Met Pro
                85                  90                  95

Cys Ala Glu Asp Tyr Leu Ser Val Val Leu Asn Gln Leu Cys Val Leu
            100                 105                 110

His Glu Lys Thr Pro Val Ser Asp Arg Val Thr Lys Cys Cys Thr Glu
        115                 120                 125

Ser Leu Val Asn Arg Arg Pro Cys Phe Ser Ala Leu Glu Val Asp Glu
130                 135                 140

Thr Tyr Val Pro Lys Glu Phe Asn Ala Glu Thr Phe Thr Phe His Ala
145                 150                 155                 160

Asp Ile Cys Thr Leu Ser Glu Lys Glu Arg Gln Ile Lys Lys Gln Thr
                165                 170                 175

Ala Leu Val Glu Leu Val Lys His Lys Pro Lys Ala Thr Lys Glu Gln
            180                 185                 190

Leu Lys Ala Val Met Asp Asp Phe Ala Ala Phe Val Glu Lys Cys Cys
        195                 200                 205

Lys Ala Asp Asp Lys Glu Thr Cys Phe Ala Glu Gly Lys Lys Leu
210                 215                 220

Val Ala Ala Ser Gln Ala Ala Leu Gly Leu Leu Glu Glu Arg Asp Cys
225                 230                 235                 240

Arg Val Ser Ser Phe Arg Val Lys Glu Asn Phe Asp Lys Ala Arg Phe
                245                 250                 255

Ser Gly Thr Trp Tyr Ala Met Ala Lys Lys Asp Pro Glu Gly Leu Phe
            260                 265                 270

Leu Gln Asp Asn Ile Val Ala Glu Phe Ser Val Asp Glu Thr Gly Gln
        275                 280                 285

Met Ser Ala Thr Ala Lys Gly Arg Val Arg Leu Leu Asn Asn Trp Asp
        290                 295                 300

Val Cys Ala Asp Met Val Gly Thr Phe Thr Asp Thr Glu Asp Pro Ala
305                 310                 315                 320

Lys Phe Lys Met Lys Tyr Trp Gly Val Ala Ser Phe Leu Gln Lys Gly
```

```
                325                 330                 335
Asn Asp Asp His Trp Ile Val Asp Thr Asp Tyr Asp Thr Tyr Ala Val
        340                 345                 350
Gln Tyr Ser Cys Arg Leu Leu Asn Leu Asp Gly Thr Cys Ala Asp Ser
        355                 360                 365
Tyr Ser Phe Val Phe Ser Arg Asp Pro Asn Gly Leu Pro Pro Glu Ala
    370                 375                 380
Gln Lys Ile Val Arg Gln Arg Gln Glu Leu Cys Leu Ala Arg Gln
385                 390                 395                 400
Tyr Arg Leu Ile Val His Asn Gly Tyr Cys Asp Gly Arg Ser Arg Asp
                405                 410                 415
Ala His Lys Ser Glu Val Ala His Arg Phe Lys Asp Leu Gly Glu Glu
            420                 425                 430
Asn Phe Lys Ala Leu Val Leu Ile Ala Phe Ala Gln Tyr Leu Gln Gln
        435                 440                 445
Cys Pro Phe Glu Asp His Val Lys Leu Val Asn Glu Val Thr Glu Phe
        450                 455                 460
Ala Lys Thr Cys Val Ala Asp Glu Ser Ala Glu Asn Cys Asp Lys Ser
465                 470                 475                 480
Leu His Thr Leu Phe Gly Asp Lys Leu Cys Thr Val Ala Thr Leu Arg
                485                 490                 495
Glu Thr Tyr Gly Glu Met Ala Asp Cys Cys Ala Lys Gln Glu Pro Glu
            500                 505                 510
Arg Asn Glu Cys Phe Leu Gln His Lys Asp Asp Asn Pro Asn Leu Pro
        515                 520                 525
Arg Leu Val Arg Pro Glu Val Asp Val Met Cys Thr Ala Phe His Asp
        530                 535                 540
Asn Glu Glu Thr Phe Leu Lys Lys Tyr Leu Tyr Glu Ile Ala Arg Arg
545                 550                 555                 560
His Pro Tyr Phe Tyr Ala Pro Glu Leu Leu Phe Phe Ala Lys Arg Tyr
                565                 570                 575
Lys Ala Ala Phe Thr Glu Cys Cys Gln Ala Ala Asp Lys Ala Ala Cys
            580                 585                 590
Leu Leu Pro Lys Leu Asp Glu Leu Arg Asp Glu Gly Lys Ala Ser Ser
        595                 600                 605
Ala Lys Gln Arg Leu His His His His His
        610                 615

<210> SEQ ID NO 10
<211> LENGTH: 407
<212> TYPE: PRT
<213> ORGANISM: Homo sapiens

<400> SEQUENCE: 10

Met Lys Trp Val Trp Ala Leu Leu Leu Leu Ala Ala Leu Gly Ser Gly
1               5                   10                  15
Arg Ala Glu Arg Asp Cys Arg Val Ser Ser Phe Arg Val Lys Glu Asn
                20                  25                  30
Phe Asp Lys Ala Arg Phe Ser Gly Thr Trp Tyr Ala Met Ala Lys Lys
            35                  40                  45
Asp Pro Glu Gly Leu Phe Leu Gln Asp Asn Ile Val Ala Glu Phe Ser
        50                  55                  60
Val Asp Glu Thr Gly Gln Met Ser Ala Thr Ala Lys Gly Arg Val Arg
65                  70                  75                  80
```

```
Leu Leu Asn Asn Trp Asp Val Cys Ala Asp Met Val Gly Thr Phe Thr
            85                  90                  95

Asp Thr Glu Asp Pro Ala Lys Phe Lys Met Lys Tyr Trp Gly Val Ala
        100                 105                 110

Ser Phe Leu Gln Lys Gly Asn Asp Asp His Trp Ile Val Asp Thr Asp
            115                 120                 125

Tyr Asp Thr Tyr Ala Val Gln Tyr Ser Cys Arg Leu Leu Asn Leu Asp
130                 135                 140

Gly Thr Cys Ala Asp Ser Tyr Ser Phe Val Phe Ser Arg Asp Pro Asn
145                 150                 155                 160

Gly Leu Pro Pro Glu Ala Gln Lys Ile Val Arg Gln Arg Gln Glu Glu
                165                 170                 175

Leu Cys Leu Ala Arg Gln Tyr Arg Leu Ile Val His Asn Gly Tyr Cys
                180                 185                 190

Asp Gly Arg Leu Glu Glu Pro Gln Asn Leu Ile Lys Gln Asn Cys
            195                 200                 205

Glu Leu Phe Glu Gln Leu Gly Glu Tyr Lys Phe Gln Asn Ala Leu Leu
    210                 215                 220

Val Arg Tyr Thr Lys Lys Val Pro Gln Val Ser Thr Pro Thr Leu Val
225                 230                 235                 240

Glu Val Ser Arg Asn Leu Gly Lys Val Gly Ser Lys Cys Cys Lys His
                245                 250                 255

Pro Glu Ala Lys Arg Met Pro Cys Ala Glu Asp Tyr Leu Ser Val Val
                260                 265                 270

Leu Asn Gln Leu Cys Val Leu His Glu Lys Thr Pro Val Ser Asp Arg
    275                 280                 285

Val Thr Lys Cys Cys Thr Glu Ser Leu Val Asn Arg Arg Pro Cys Phe
290                 295                 300

Ser Ala Leu Glu Val Asp Glu Thr Tyr Val Pro Lys Glu Phe Asn Ala
305                 310                 315                 320

Glu Thr Phe Thr Phe His Ala Asp Ile Cys Thr Leu Ser Glu Lys Glu
                325                 330                 335

Arg Gln Ile Lys Lys Gln Thr Ala Leu Val Glu Leu Val Lys His Lys
                340                 345                 350

Pro Lys Ala Thr Lys Glu Gln Leu Lys Ala Val Met Asp Asp Phe Ala
                355                 360                 365

Ala Phe Val Glu Lys Cys Cys Lys Ala Asp Asp Lys Glu Thr Cys Phe
                370                 375                 380

Ala Glu Glu Gly Lys Lys Leu Val Ala Ala Ser Gln Ala Ala Leu Gly
385                 390                 395                 400

Leu His His His His His His
                405

<210> SEQ ID NO 11
<211> LENGTH: 425
<212> TYPE: PRT
<213> ORGANISM: Homo sapiens

<400> SEQUENCE: 11

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
                20                  25                  30

Pro Gln Asn Leu Ile Lys Gln Asn Cys Glu Leu Phe Glu Gln Leu Gly
            35                  40                  45
```

Glu Tyr Lys Phe Gln Asn Ala Leu Leu Val Arg Tyr Thr Lys Lys Val
 50                  55                  60

Pro Gln Val Ser Thr Pro Thr Leu Val Glu Val Ser Arg Asn Leu Gly
 65                  70                  75                  80

Lys Val Gly Ser Lys Cys Cys Lys His Pro Glu Ala Lys Arg Met Pro
                 85                  90                  95

Cys Ala Glu Asp Tyr Leu Ser Val Val Leu Asn Gln Leu Cys Val Leu
             100                 105                 110

His Glu Lys Thr Pro Val Ser Asp Arg Val Thr Lys Cys Cys Thr Glu
         115                 120                 125

Ser Leu Val Asn Arg Arg Pro Cys Phe Ser Ala Leu Glu Val Asp Glu
     130                 135                 140

Thr Tyr Val Pro Lys Glu Phe Asn Ala Glu Thr Phe Thr Phe His Ala
145                 150                 155                 160

Asp Ile Cys Thr Leu Ser Glu Lys Glu Arg Gln Ile Lys Lys Gln Thr
                165                 170                 175

Ala Leu Val Glu Leu Val Lys His Lys Pro Lys Ala Thr Lys Glu Gln
            180                 185                 190

Leu Lys Ala Val Met Asp Asp Phe Ala Ala Phe Val Glu Lys Cys Cys
        195                 200                 205

Lys Ala Asp Asp Lys Glu Thr Cys Phe Ala Glu Glu Gly Lys Lys Leu
    210                 215                 220

Val Ala Ala Ser Gln Ala Ala Leu Gly Leu Leu Glu Glu Arg Asp Cys
225                 230                 235                 240

Arg Val Ser Ser Phe Arg Val Lys Glu Asn Phe Asp Lys Ala Arg Phe
                245                 250                 255

Ser Gly Thr Trp Tyr Ala Met Ala Lys Lys Asp Pro Glu Gly Leu Phe
            260                 265                 270

Leu Gln Asp Asn Ile Val Ala Glu Phe Ser Val Asp Glu Thr Gly Gln
        275                 280                 285

Met Ser Ala Thr Ala Lys Gly Arg Val Arg Leu Leu Asn Asn Trp Asp
    290                 295                 300

Val Cys Ala Asp Met Val Gly Thr Phe Thr Asp Thr Glu Asp Pro Ala
305                 310                 315                 320

Lys Phe Lys Met Lys Tyr Trp Gly Val Ala Ser Phe Leu Gln Lys Gly
                325                 330                 335

Asn Asp Asp His Trp Ile Val Asp Thr Asp Tyr Asp Thr Tyr Ala Val
            340                 345                 350

Gln Tyr Ser Cys Arg Leu Leu Asn Leu Asp Gly Thr Cys Ala Asp Ser
        355                 360                 365

Tyr Ser Phe Val Phe Ser Arg Asp Pro Asn Gly Leu Pro Pro Glu Ala
    370                 375                 380

Gln Lys Ile Val Arg Gln Arg Gln Glu Glu Leu Cys Leu Ala Arg Gln
385                 390                 395                 400

Tyr Arg Leu Ile Val His Asn Gly Tyr Cys Asp Gly Arg Ser Glu Arg
                405                 410                 415

Asn Leu Leu His His His His His
            420                 425

<210> SEQ ID NO 12
<211> LENGTH: 800
<212> TYPE: PRT
<213> ORGANISM: Homo sapiens

```
<400> SEQUENCE: 12

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
                20                  25                  30

His Arg Phe Lys Asp Leu Gly Glu Glu Asn Phe Lys Ala Leu Val Leu
            35                  40                  45

Ile Ala Phe Ala Gln Tyr Leu Gln Gln Cys Pro Phe Glu Asp His Val
50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
            115                 120                 125

His Lys Asp Asp Asn Pro Asn Leu Pro Arg Leu Val Arg Pro Glu Val
            130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
            195                 200                 205

Leu Arg Asp Glu Gly Lys Ala Ser Ser Ala Lys Gln Arg Leu Lys Cys
            210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
            275                 280                 285

Cys Glu Asn Gln Asp Ser Ile Ser Ser Lys Leu Lys Glu Cys Cys Glu
            290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
            355                 360                 365

Leu Leu Leu Arg Leu Ala Lys Thr Tyr Glu Thr Thr Leu Glu Lys Cys
            370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415
```

Glu Leu Phe Glu Gln Leu Gly Glu Tyr Lys Phe Gln Asn Ala Leu Leu
                420                 425                 430

Val Arg Tyr Thr Lys Lys Val Pro Gln Val Ser Thr Pro Thr Leu Val
            435                 440                 445

Glu Val Ser Arg Asn Leu Gly Lys Val Gly Ser Lys Cys Cys Lys His
450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
        515                 520                 525

Glu Thr Phe Thr Phe His Ala Asp Ile Cys Thr Leu Ser Glu Lys Glu
    530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
        595                 600                 605

Leu Leu Glu Glu Arg Asp Cys Arg Val Ser Ser Phe Arg Val Lys Glu
    610                 615                 620

Asn Phe Asp Lys Ala Arg Phe Ser Gly Thr Trp Tyr Ala Met Ala Lys
625                 630                 635                 640

Lys Asp Pro Glu Gly Leu Phe Leu Gln Asp Asn Ile Val Ala Glu Phe
                645                 650                 655

Ser Val Asp Glu Thr Gly Gln Met Ser Ala Thr Ala Lys Gly Arg Val
            660                 665                 670

Arg Leu Leu Asn Asn Trp Asp Val Cys Ala Asp Met Val Gly Thr Phe
        675                 680                 685

Thr Asp Thr Glu Asp Pro Ala Lys Phe Lys Met Lys Tyr Trp Gly Val
    690                 695                 700

Ala Ser Phe Leu Gln Lys Gly Asn Asp Asp His Trp Ile Val Asp Thr
705                 710                 715                 720

Asp Tyr Asp Thr Tyr Ala Val Gln Tyr Ser Cys Arg Leu Leu Asn Leu
                725                 730                 735

Asp Gly Thr Cys Ala Asp Ser Tyr Ser Phe Val Phe Ser Arg Asp Pro
            740                 745                 750

Asn Gly Leu Pro Pro Glu Ala Gln Lys Ile Val Arg Gln Arg Gln Glu
        755                 760                 765

Glu Leu Cys Leu Ala Arg Gln Tyr Arg Leu Ile Val His Asn Gly Tyr
    770                 775                 780

Cys Asp Gly Arg Ser Glu Arg Asn Leu Leu His His His His His His
785                 790                 795                 800

<210> SEQ ID NO 13
<211> LENGTH: 788
<212> TYPE: PRT
<213> ORGANISM: Homo sapiens

<400> SEQUENCE: 13

```
Met Lys Trp Val Trp Ala Leu Leu Leu Ala Ala Leu Gly Ser Gly
1               5                   10                  15

Arg Ala Glu Arg Asp Cys Arg Val Ser Ser Phe Arg Val Lys Glu Asn
            20                  25                  30

Phe Asp Lys Ala Arg Phe Ser Gly Thr Trp Tyr Ala Met Ala Lys Lys
            35                  40                  45

Asp Pro Glu Gly Leu Phe Leu Gln Asp Asn Ile Val Ala Glu Phe Ser
        50                  55                  60

Val Asp Glu Thr Gly Gln Met Ser Ala Thr Ala Lys Gly Arg Val Arg
65                  70                  75                  80

Leu Leu Asn Asn Trp Asp Val Cys Ala Asp Met Val Gly Thr Phe Thr
                85                  90                  95

Asp Thr Glu Asp Pro Ala Lys Phe Lys Met Lys Tyr Trp Gly Val Ala
            100                 105                 110

Ser Phe Leu Gln Lys Gly Asn Asp Asp His Trp Ile Val Asp Thr Asp
        115                 120                 125

Tyr Asp Thr Tyr Ala Val Gln Tyr Ser Cys Arg Leu Leu Asn Leu Asp
        130                 135                 140

Gly Thr Cys Ala Asp Ser Tyr Ser Phe Val Phe Ser Arg Asp Pro Asn
145                 150                 155                 160

Gly Leu Pro Pro Glu Ala Gln Lys Ile Val Arg Gln Arg Gln Glu Glu
                165                 170                 175

Leu Cys Leu Ala Arg Gln Tyr Arg Leu Ile Val His Asn Gly Tyr Cys
            180                 185                 190

Asp Gly Arg Leu Glu Asp Ala His Lys Ser Glu Val Ala His Arg Phe
        195                 200                 205

Lys Asp Leu Gly Glu Glu Asn Phe Lys Ala Leu Val Leu Ile Ala Phe
    210                 215                 220

Ala Gln Tyr Leu Gln Gln Cys Pro Phe Glu Asp His Val Lys Leu Val
225                 230                 235                 240

Asn Glu Val Thr Glu Phe Ala Lys Thr Cys Val Ala Asp Glu Ser Ala
                245                 250                 255

Glu Asn Cys Asp Lys Ser Leu His Thr Leu Phe Gly Asp Lys Leu Cys
            260                 265                 270

Thr Val Ala Thr Leu Arg Glu Thr Tyr Gly Glu Met Ala Asp Cys Cys
        275                 280                 285

Ala Lys Gln Glu Pro Glu Arg Asn Glu Cys Phe Leu Gln His Lys Asp
    290                 295                 300

Asp Asn Pro Asn Leu Pro Arg Leu Val Arg Pro Glu Val Asp Val Met
305                 310                 315                 320

Cys Thr Ala Phe His Asp Asn Glu Glu Thr Phe Leu Lys Lys Tyr Leu
                325                 330                 335

Tyr Glu Ile Ala Arg Arg His Pro Tyr Phe Tyr Ala Pro Glu Leu Leu
            340                 345                 350

Phe Phe Ala Lys Arg Tyr Lys Ala Ala Phe Thr Glu Cys Cys Gln Ala
        355                 360                 365

Ala Asp Lys Ala Ala Cys Leu Leu Pro Lys Leu Asp Glu Leu Arg Asp
    370                 375                 380

Glu Gly Lys Ala Ser Ser Ala Lys Gln Arg Leu Lys Cys Ala Ser Leu
385                 390                 395                 400

Gln Lys Phe Gly Glu Arg Ala Phe Lys Ala Trp Ala Val Ala Arg Leu
                405                 410                 415
```

```
Ser Gln Arg Phe Pro Lys Ala Glu Phe Ala Glu Val Ser Lys Leu Val
            420                 425                 430

Thr Asp Leu Thr Lys Val His Thr Glu Cys Cys His Gly Asp Leu Leu
        435                 440                 445

Glu Cys Ala Asp Asp Arg Ala Asp Leu Ala Lys Tyr Ile Cys Glu Asn
    450                 455                 460

Gln Asp Ser Ile Ser Ser Lys Leu Lys Glu Cys Cys Glu Lys Pro Leu
465                 470                 475                 480

Leu Glu Lys Ser His Cys Ile Ala Glu Val Glu Asn Asp Glu Met Pro
                485                 490                 495

Ala Asp Leu Pro Ser Leu Ala Ala Asp Phe Val Glu Ser Lys Asp Val
            500                 505                 510

Cys Lys Asn Tyr Ala Glu Ala Lys Asp Val Phe Leu Gly Met Phe Leu
        515                 520                 525

Tyr Glu Tyr Ala Arg Arg His Pro Asp Tyr Ser Val Val Leu Leu Leu
    530                 535                 540

Arg Leu Ala Lys Thr Tyr Glu Thr Thr Leu Glu Lys Cys Cys Ala Ala
545                 550                 555                 560

Ala Asp Pro His Glu Cys Tyr Ala Lys Val Phe Asp Glu Phe Lys Pro
                565                 570                 575

Leu Val Glu Glu Pro Gln Asn Leu Ile Lys Gln Asn Cys Glu Leu Phe
            580                 585                 590

Glu Gln Leu Gly Glu Tyr Lys Phe Gln Asn Ala Leu Leu Val Arg Tyr
        595                 600                 605

Thr Lys Lys Val Pro Gln Val Ser Thr Pro Thr Leu Val Glu Val Ser
    610                 615                 620

Arg Asn Leu Gly Lys Val Gly Ser Lys Cys Cys Lys His Pro Glu Ala
625                 630                 635                 640

Lys Arg Met Pro Cys Ala Glu Asp Tyr Leu Ser Val Val Leu Asn Gln
                645                 650                 655

Leu Cys Val Leu His Glu Lys Thr Pro Val Ser Asp Arg Val Thr Lys
            660                 665                 670

Cys Cys Thr Glu Ser Leu Val Asn Arg Arg Pro Cys Phe Ser Ala Leu
        675                 680                 685

Glu Val Asp Glu Thr Tyr Val Pro Lys Glu Phe Asn Ala Glu Thr Phe
    690                 695                 700

Thr Phe His Ala Asp Ile Cys Thr Leu Ser Glu Lys Glu Arg Gln Ile
705                 710                 715                 720

Lys Lys Gln Thr Ala Leu Val Glu Leu Val Lys His Lys Pro Lys Ala
                725                 730                 735

Thr Lys Glu Gln Leu Lys Ala Val Met Asp Asp Phe Ala Ala Phe Val
            740                 745                 750

Glu Lys Cys Cys Lys Ala Asp Asp Lys Glu Thr Cys Phe Ala Glu Glu
        755                 760                 765

Gly Lys Lys Leu Val Ala Ala Ser Gln Ala Ala Leu Gly Leu His His
    770                 775                 780

His His His His
785

<210> SEQ ID NO 14
<211> LENGTH: 1842
<212> TYPE: DNA
<213> ORGANISM: Homo sapiens
```

<400> SEQUENCE: 14

```
atgaagtggg taacctttat ttccttctt tttctcttta gctcggctta ttccaggggt      60
gtgtttcgtc gagatgcaca caagagtgag gttgctcatc ggtttaaaga tttgggagaa    120
gaaaatttca agccttggt gttgattgcc tttgctcagt atcttcagca gtgtccattt     180
gaagatcatg taaaattagt gaatgaagta actgaatttg caaaaacatg tgttgctgat   240
gagtcagctg aaaattgtga caaatcactt catacccttt ttggagacaa attatgcaca   300
gttgcaactc ttcgtgaaac ctatggtgaa atggctgact gctgtgcaaa acaagaacct   360
gagagaaatg aatgcttctt gcaacacaaa gatgacaacc caaacctccc ccgattggtg   420
agaccagagg ttgatgtgat gtgcactgct tttcatgaca atgaagagac attttttgaaa 480
aaatacttat atgaaattgc cagaagacat ccttactttt atgccccgga actccttttc   540
tttgctaaaa ggtataaagc tgcttttaca gaatgttgcc aagctgctga taaagctgcc   600
tgcctgttgc caaagctcga tgaacttcgg gatgaaggga aggcttcgtc tgccaaacag   660
agactccaat tggagcgcga ctgccgagtg agcagcttcc gagtcaagga gaacttcgac   720
aaggctcgct tctctgggac ctggtacgcc atggccaaga aggaccccga gggcctcttt   780
ctgcaggaca acatcgtcgc ggagttctcc gtggacgaga ccggccagat gagcgccaca   840
gccaagggcc agtccgtctt tttgaataac tgggacgtgt cgcagacat ggtgggcacc    900
ttcacagaca ccgaggaccc tgccaagttc aagatgaagt actggggcgt agcctccttt   960
ctccagaaag gaaatgatga ccactggatc gtcgacacag actacgacac gtatgccgtg  1020
cagtactcct gccgcctcct gaactcgat ggcacctgtg ctgacagcta ctccttcgtg   1080
ttttcccggg accccaacgg cctgccccca gaagcgcaga gattgtaag gcagcggcag    1140
gaggagctgt gcctggccag gcagtacagg ctgatcgtcc acaacggtta ctgcgatggc  1200
agactcgagg aagagcctca gaatttaatc aaacaaaatt gtgagctttt tgagcagctt  1260
ggagagtaca aattccagaa tgcgctatta gttcgttaca ccaagaaagt accccaagtg  1320
tcaactccaa ctcttgtaga ggtctcaaga aacctaggaa aagtgggcag caaatgttgt  1380
aaacatcctg aagcaaaaag aatgcctgt gcagaagact atctatccgt ggtcctgaac   1440
cagttatgtg tgttgcatga gaaaacgcca gtaagtgaca gagtcaccaa atgctgcaca  1500
gaatccttgg tgaacaggcg accatgcttt tcagctctgg aagtcgatga acatacgtt   1560
cccaaagagt ttaatgctga acattcacc ttccatgcag atatatgcac actttctgag  1620
aaggagagac aaatcaagaa acaaactgca cttgttgagc tcgtgaaaca caagcccaag  1680
gcaacaaaag agcaactgaa agctgttatg gatgatttcg cagcttttgt agagaagtgc  1740
tgcaaggctg acgataagga gacctgcttt gccgaggagg gtaaaaaact tgttgctgca  1800
agtcaagctg ccttaggctt acatcatcat catcatcatt aa                      1842
```

<210> SEQ ID NO 15
<211> LENGTH: 1860
<212> TYPE: DNA
<213> ORGANISM: Homo sapiens

<400> SEQUENCE: 15

```
atgaagtggg taacctttat ttccttctt tttctcttta gctcggctta ttccagggt      60
gtgtttcgtc gagatgcaca caagcaattg gaagagcctc agaatttaat caaacaaaat   120
tgtgagcttt ttgagcagct tggagagtac aaattccaga tgcgctatt agttcgttac    180
accaagaaag taccccaagt gtcaactcca actcttgtag aggtctcaag aaacctagga   240
```

```
aaagtgggca gcaaatgttg taaacatcct gaagcaaaaa gaatgccctg tgcagaagac    300
tatctatccg tggtcctgaa ccagttatgt gtgttgcatg agaaaacgcc agtaagtgac    360
agagtcacca aatgctgcac agaatccttg gtgaacaggc gaccatgctt ttcagctctg    420
gaagtcgatg aaacatacgt tcccaaagag tttaatgctg aaacattcac cttccatgca    480
gatatatgca cactttctga aaggagaga caaatcaaga aacaaactgc acttgttgag    540
ctcgtgaaac acaagcccaa ggcaacaaaa gagcaactga aagctgttat ggatgatttc    600
gcagcttttg tagagaagtg ctgcaaggct gacgataagg agacctgctt tgccgaggag    660
ggtaaaaaac ttgttgctgc aagtcaagct gccttaggct tactcgagga gcgcgactgc    720
cgagtgagca gcttccgagt caaggagaac ttcgacaagg ctcgcttctc tgggacctgg    780
tacgccatgg ccaagaagga ccccgagggc ctctttctgc aggacaacat cgtcgcggag    840
ttctccgtgg acgagaccgg ccagatgagc gccacagcca agggccgagt ccgtcttttg    900
aataactggg acgtgtgcgc agacatggtg ggcaccttca cagacaccga ggaccctgcc    960
aagttcaaga tgaagtactg gggcgtagcc tcctttctcc agaaaggaaa tgatgaccac   1020
tggatcgtcg acacagacta cgacacgtat gccgtgcagt actcctgccg cctcctgaac   1080
ctcgatggca cctgtgctga cagctactcc ttcgtgtttt ccgggaccc caacggcctg   1140 cccccagaag cgcagaagat tgtaaggcag cggcaggagg agctgtgcct ggccaggcag   1200
tacaggctga tcgtccacaa cggttactgc gatggcagat ctagagatgc acacaagagt   1260
gaggttgctc atcggtttaa agatttggga gaagaaaatt tcaaagcctt ggtgttgatt   1320
gcctttgctc agtatcttca gcagtgtcca tttgaagatc atgtaaaatt agtgaatgaa   1380
gtaactgaat ttgcaaaaac atgtgttgct gatgagtcag ctgaaaattg tgacaaatca   1440 cttcatacccc tttttggaga caaattatgc acagttgcaa ctcttcgtga aacctatggt   1500
gaaatggctg actgctgtgc aaaacaagaa cctgagagaa atgaatgctt cttgcaacac   1560
aaagatgaca acccaaacct ccccgattg gtgagaccag aggttgatgt gatgtgcact   1620
gcttttcatg acaatgaaga gacatttttg aaaaaatact tatatgaaat tgccagaaga   1680
catccttact tttatgcccc ggaactcctt ttctttgcta aaaggtataa agctgctttt   1740
acagaatgtt gccaagctgc tgataaagct gcctgcctgt tgccaaagct cgatgaactt   1800
cgggatgaag ggaaggcttc gtctgccaaa cagagactcc atcatcatca tcatcattaa   1860

<210> SEQ ID NO 16
<211> LENGTH: 1224
<212> TYPE: DNA
<213> ORGANISM: Homo sapiens

<400> SEQUENCE: 16
atgaagtggg tgtgggcgct cttgctgttg gcggcgctgg gcagcggccg cgcggagcgc     60
gactgccgag tgagcagctt ccgagtcaag gagaacttcg acaaggctcg cttctctggg    120
acctggtacg ccatggccaa gaaggacccc gagggcctct ttctgcagga caacatcgtc    180
gcggagttct ccgtggacga gaccggccag atgagcgcca cagccaaggg ccgagtccgt    240
cttttgaata actgggacgt gtgcgcagac atggtgggca ccttcacaga caccgaggac    300
cctgccaagt tcaagatgaa gtactggggc gtagcctcct ttctccagaa aggaaatgat    360
gaccactgga tcgtcgacac agactacgac acgtatgccg tgcagtactc ctgccgcctc    420
ctgaacctcg atggcacctg tgctgacagc tactccttcg tgttttcccg ggaccccaac    480
```

| | |
|---|---:|
| ggcctgcccc cagaagcgca gaagattgta aggcagcggc aggaggagct gtgcctggcc | 540 |
| aggcagtaca ggctgatcgt ccacaacggt tactgcgatg gcagactcga ggaagagcct | 600 |
| cagaatttaa tcaaacaaaa ttgtgagctt tttgagcagc ttggagagta caaattccag | 660 |
| aatgcgctat tagttcgtta caccaagaaa gtaccccaag tgtcaactcc aactcttgta | 720 |
| gaggtctcaa gaaacctagg aaaagtgggc agcaaatgtt gtaaacatcc tgaagcaaaa | 780 |
| agaatgccct gtcagaagac tatctatccg tggtcctga accagttatg tgtgttgcat | 840 |
| gagaaaacgc cagtaagtga cagagtcacc aaatgctgca cagaatcctt ggtgaacagg | 900 |
| cgaccatgct ttcagctctg gaagtcgat gaaacatacg ttcccaaaga gtttaatgct | 960 |
| gaaacattca ccttccatgc agatatatgc acactttctg agaaggagag acaaatcaag | 1020 |
| aaacaaactg cacttgttga gctcgtgaaa cacaagccca aggcaacaaa agagcaactg | 1080 |
| aaagctgtta tggatgattt cgcagctttt gtagagaagt gctgcaaggc tgacgataag | 1140 |
| gagacctgct ttgccgagga gggtaaaaaa cttgttgctg caagtcaagc tgccttaggc | 1200 |
| ttacatcatc atcatcatca ttaa | 1224 |

<210> SEQ ID NO 17
<211> LENGTH: 1278
<212> TYPE: DNA
<213> ORGANISM: Homo sapiens

<400> SEQUENCE: 17

| | |
|---|---:|
| atgaagtggg taacctttat ttcccttctt tttctcttta gctcggctta ttccaggggt | 60 |
| gtgtttcgtc gagatgcaca caagcaattg gaagagcctc agaatttaat caaacaaaat | 120 |
| tgtgagcttt ttgagcagct tggagagtac aaattccaga atgcgctatt agttcgttac | 180 |
| accaagaaag taccccaagt gtcaactcca actcttgtag aggtctcaag aaacctagga | 240 |
| aaagtgggca gcaaatgttg taaacatcct gaagcaaaaa gaatgccctg tcagaagac | 300 |
| tatctatccg tggtcctgaa ccagttatgt gtgttcatg agaaaacgcc agtaagtgac | 360 |
| agagtcacca aatgctgcac agaatccttg gtgaacaggc gaccatgctt tcagctctg | 420 |
| gaagtcgatg aaacatacgt tcccaaagag tttaatgctg aaacattcac cttccatgca | 480 |
| gatatatgca cactttctga aggagagaca aatcaagaa acaaactgc acttgttgag | 540 |
| ctcgtgaaac acaagcccaa ggcaacaaaa gagcaactga aagctgttat ggatgatttc | 600 |
| gcagcttttg tagagaagtg ctgcaaggct gacgataagg agacctgctt tgccgaggag | 660 |
| ggtaaaaaac ttgttgctgc aagtcaagct gccttaggct tactcgagga gcgcgactgc | 720 |
| cgagtgagca gcttccgagt caaggagaac ttcgacaagg ctcgcttctc tgggacctgg | 780 |
| tacgccatgg ccaagaagga ccccgagggc ctctttctgc aggacaacat cgtcgcggag | 840 |
| ttctccgtgg acgagaccgg ccagatgagc gccacagcca agggccgagt ccgtctttg | 900 |
| aataactggg acgtgtgcgc agacatggtg gcaccttca cagacaccga ggaccctgcc | 960 |
| aagttcaaga tgaagtactg gggcgtagcc tcctttctcc agaaaggaaa tgatgaccac | 1020 |
| tggatcgtcg acacagacta cgacacgtat gccgtgcagt actcctgccg cctcctgaac | 1080 |
| ctcgatggca cctgtgctga cagctactcc ttcgtgtttt cccgggaccc caacggcctg | 1140 |
| cccccagaag cgcagaagat tgtaaggcag cggcaggagg agctgtgcct ggccaggcag | 1200 |
| tacaggctga tcgtccacaa cggttactgc gatggcagat cagaaagaaa ccttttgcat | 1260 |
| catcatcatc atcattag | 1278 |

```
<210> SEQ ID NO 18
<211> LENGTH: 2403
<212> TYPE: DNA
<213> ORGANISM: Homo sapiens

<400> SEQUENCE: 18
atgaagtggg taacctttat ttcccttctt tttctcttta gctcggctta ttccaggggt      60
gtgtttcgtc gagatgcaca caagagtgag gttgctcatc ggtttaaaga tttgggagaa     120
gaaaatttca aagccttggt gttgattgcc tttgctcagt atcttcagca gtgtccattt     180
gaagatcatg taaaattagt gaatgaagta actgaatttg caaaaacatg tgttgctgat     240
gagtcagctg aaaattgtga caaatcactt catacccttt ttggagacaa attatgcaca     300
gttgcaactc ttcgtgaaac ctatggtgaa atggctgact gctgtgcaaa acaagaacct     360
gagagaaatg aatgcttctt gcaacacaaa gatgacaacc caaacctccc ccgattggtg     420
agaccagagg ttgatgtgat gtgcactgct tttcatgaca atgaagagac attttttgaaa    480
aaatacttat atgaaattgc agaagacatc cttactttt atgccccgga actccttttc      540
tttgctaaaa ggtataaagc tgcttttaca gaatgttgcc aagctgctga taaagctgcc     600
tgcctgttgc caaagctcga tgaacttcgg gatgaaggga aggcttcgtc tgccaaacag     660
agactcaagt gtgccagtct ccaaaaattt ggagaaagag ctttcaaagc atgggcagta     720
gctcgcctga ccagagatt cccaaagct gagtttgcag aagtttccaa gttagtgaca      780
gatcttacca agtccacac ggaatgctgc catggagatc tgcttgaatg tgctgatgac     840
agggcggacc ttgccaagta tatctgtgaa aatcaagatt cgatctccag taaactgaag     900
gaatgctgtg aaaaacctct gttggaaaaa tcccactgca ttgccgaagt ggaaaatgat     960
gagatgcctg ctgacttgcc ttcattagct gctgattttg ttgaaagtaa ggatgtttgc    1020
aaaaactatg ctgaggcaaa ggatgtcttc ctgggcatgt ttttgtatga atatgcaaga    1080
aggcatcctg attactctgt cgtgctgctg ctgagacttg ccaagacata tgaaaccact    1140
ctagagaagt gctgtgccgc tgcagatcct catgaatgct atgccaaagt gttcgatgaa    1200
tttaaacctc ttgtggaaga gcctcagaat ttaatcaaac aaaattgtga gcttttttgag    1260
cagcttggag agtacaaatt ccagaatgcg ctattagttc gttacaccaa gaaagtaccc    1320
caagtgtcaa ctccaactct tgtagaggtc tcaagaaacc taggaaaagt gggcagcaaa    1380
tgttgtaaac atcctgaagc aaaaagaatg ccctgtgcag aagactatct atccgtggtc    1440
ctgaaccagt tatgtgtgtt gcatgagaaa acgccagtaa gtgacagagt caccaaatgc    1500
tgcacagaat ccttggtgaa caggcgacca tgcttttcag ctctggaagt cgatgaaaca    1560
tacgttccca agagtttaa tgctgaaaca ttcaccttcc atgcagatat atgcacactt    1620
tctgagaagg agagacaaat caagaaacaa actgcacttg ttgagctcgt gaaacacaag    1680
cccaaggcaa caaagagca actgaaagct gttatggatg atttcgcagc ttttgtagag    1740
aagtgctgca aggctgacga taaggagacc tgctttgccg aggagggtaa aaaacttgtt    1800
gctgcaagtc aagctgcctt aggcttactc gaggagcgcg actgccgagt gagcagcttc    1860
cgagtcaagg agaacttcga caaggctcgc ttctctggga cctggtacgc catggccaag    1920
aaggaccccg agggcctctt tctgcaggac aacatcgtcg cggagttctc cgtggacgag    1980
accggccaga tgagcgccac agccaagggc cgagtccgtc tttgaataa ctgggacgtg    2040
tgcgcagaca tggtgggcac cttcacagac accgaggacc ctgccaagtt caagatgaag    2100
tactggggcg tagcctcctt tctccagaaa ggaaatgatg accactggat cgtcgacaca    2160
```

| | |
|---|---|
| gactacgaca cgtatgccgt gcagtactcc tgccgcctcc tgaacctcga tggcacctgt | 2220 |
| gctgacagct actccttcgt gttttcccgg gaccccaacg gcctgccccc agaagcgcag | 2280 |
| aagattgtaa ggcagcggca ggaggagctg tgcctggcca ggcagtacag gctgatcgtc | 2340 |
| cacaacggtt actgcgatgg cagatcagaa agaaaccttt tgcatcatca tcatcatcat | 2400 |
| tag | 2403 |

<210> SEQ ID NO 19
<211> LENGTH: 2367
<212> TYPE: DNA
<213> ORGANISM: Homo sapiens

<400> SEQUENCE: 19

| | |
|---|---|
| atgaagtggg tgtgggcgct cttgctgttg gcggcgctgg gcagcggccg cgcggagcgc | 60 |
| gactgccgag tgagcagctt ccgagtcaag gagaacttcg acaaggctcg cttctctggg | 120 |
| acctggtacg ccatggccaa gaaggacccc gagggcctct ttctgcagga caacatcgtc | 180 |
| gcggagttct ccgtggacga gaccggccag atgagcgcca cagccaaggg ccgagtccgt | 240 |
| cttttgaata ctgggacgt gtgcgcagac atggtgggca ccttcacaga caccgaggac | 300 |
| cctgccaagt tcaagatgaa gtactggggc gtagcctcct tctccagaa aggaaatgat | 360 |
| gaccactgga tcgtcgacac agactacgac acgtatgccg tgcagtactc ctgccgcctc | 420 |
| ctgaacctcg atggcacctg tgctgacagc tactccttcg tgttttcccg ggaccccaac | 480 |
| ggcctgcccc agaagcgcag aagattgta aggcagcggc aggaggagct gtgcctggcc | 540 |
| aggcagtaca ggctgatcgt ccacaacggt tactgcgatg gcagactcga ggatgcacac | 600 |
| aagagtgagg ttgctcatcg gtttaaagat ttgggagaag aaaatttcaa gccttggtg | 660 |
| ttgattgcct ttgctcagta tcttcagcag tgtccatttg aagatcatgt aaaattagtg | 720 |
| aatgaagtaa ctgaatttgc aaaaacatgt gttgctgatg agtcagctga aaattgtgac | 780 |
| aaatcacttc ataccctttt tggagacaaa ttatgcacag ttgcaactct tcgtgaaacc | 840 |
| tatggtgaaa tggctgactg ctgtgcaaaa caagaacctg agagaatga atgcttcttg | 900 |
| caacacaaag atgacaaccc aaacctcccc cgattggtga ccagaggt tgatgtgatg | 960 |
| tgcactgctt tcatgacaa tgaagagaca ttttgaaaa atacttata tgaaattgcc | 1020 |
| agaagacatc cttacttta tgccccggaa ctcctttct ttgctaaaag gtataaagct | 1080 |
| gcttttacag aatgttgcca agctgctgat aaagctgcct gcctgttgcc aaagctcgat | 1140 |
| gaacttcggg atgaagggaa ggcttcgtct gccaaacaga gactcaagtg tgccagtctc | 1200 |
| caaaaatttg gagaaagagc tttcaaagca tgggcagtag ctcgcctgag ccagagattt | 1260 |
| cccaaagctg agtttgcaga agtttccaag ttagtgacag atcttaccaa gtccacacg | 1320 |
| gaatgctgcc atggagatct gcttgaatgt gctgatgaca gggcggacct tgccaagtat | 1380 |
| atctgtgaaa atcaagattc gatctccagt aaactgaagg aatgctgtga aaacctctg | 1440 |
| ttggaaaaat cccactgcat tgccgaagtg gaaaatgatg agatgcctgc tgacttgcct | 1500 |
| tcattagctg ctgattttgt tgaaagtaag gatgtttgca aaaactatgc tgaggcaaag | 1560 |
| gatgtcttcc tgggcatgtt tttgtatgaa tatgcaagaa ggcatcctga ttactctgtc | 1620 |
| gtgctgctgc tgagacttgc caagacatat gaaaccactc tagagaagtg ctgtgccgct | 1680 |
| gcagatcctc atgaatgcta tgccaaagtg ttcgatgaat ttaaacctct gtgtgaagag | 1740 |
| cctcagaatt taatcaaaca aaattgtgag cttttgagc agcttggaga gtacaaattc | 1800 |
| cagaatgcgc tattagttcg ttacaccaag aaagtacccc aagtgtcaac tccaactctt | 1860 |

-continued

```
gtagaggtct caagaaacct aggaaaagtg ggcagcaaat gttgtaaaca tcctgaagca    1920
aaaagaatgc cctgtgcaga agactatcta tccgtggtcc tgaaccagtt atgtgtgttg    1980
catgagaaaa cgccagtaag tgacagagtc accaaatgct gcacagaatc cttggtgaac    2040
aggcgaccat gcttttcagc tctggaagtc gatgaaacat acgttcccaa agagtttaat    2100
gctgaaacat tcaccttcca tgcagatata tgcacacttt ctgagaagga gacaaatc     2160 aagaaacaaa ctgcacttgt tgagctcgtg aaacacaagc ccaaggcaac aaaagagcaa    2220
ctgaaagctg ttatggatga tttcgcagct tttgtagaga agtgctgcaa ggctgacgat    2280
aaggagacct gctttgccga ggagggtaaa aaacttgttg ctgcaagtca agctgcctta    2340
ggcttacatc atcatcatca tcattaa                                        2367
```

<210> SEQ ID NO 20
<211> LENGTH: 32
<212> TYPE: DNA
<213> ORGANISM: Artificial Sequence
<220> FEATURE:
<223> OTHER INFORMATION: sense primer for albumin domain I in rat

<400> SEQUENCE: 20

```
ggggtacccc accatgaagt gggtaacctt tc                                    32
```

<210> SEQ ID NO 21
<211> LENGTH: 27
<212> TYPE: DNA
<213> ORGANISM: Artificial Sequence
<220> FEATURE:
<223> OTHER INFORMATION: antisense primer for albumin domain I in rat

<400> SEQUENCE: 21

```
ccccaattgc atcctctgac ggacagc                                         27
```

<210> SEQ ID NO 22
<211> LENGTH: 27
<212> TYPE: DNA
<213> ORGANISM: Artificial Sequence
<220> FEATURE:
<223> OTHER INFORMATION: sense primer for RBP(55-585) in rat

<400> SEQUENCE: 22

```
gggcaattgg agcgcgactg cagggtg                                         27
```

<210> SEQ ID NO 23
<211> LENGTH: 27
<212> TYPE: DNA
<213> ORGANISM: Artificial Sequence
<220> FEATURE:
<223> OTHER INFORMATION: antisense primer for RBP(55-585) in rat

<400> SEQUENCE: 23

```
cccctcgagt ctgctttgac agtaacc                                         27
```

<210> SEQ ID NO 24
<211> LENGTH: 27
<212> TYPE: DNA
<213> ORGANISM: Artificial Sequence
<220> FEATURE:
<223> OTHER INFORMATION: sense primer for albumin domain III in rat

<400> SEQUENCE: 24

```
gggctcgagg aagaacctaa gaacttg                                         27
```

```
<210> SEQ ID NO 25
<211> LENGTH: 48
<212> TYPE: DNA
<213> ORGANISM: Artificial Sequence
<220> FEATURE:
<223> OTHER INFORMATION: antisense primer for albumin domain III in rat

<400> SEQUENCE: 25
ggctctagat taatgatgat gatgatgatg ggctaaggct tctttgct                        48

<210> SEQ ID NO 26
<211> LENGTH: 30
<212> TYPE: DNA
<213> ORGANISM: Artificial Sequence
<220> FEATURE:
<223> OTHER INFORMATION: sense primer for RBP(1-585) in rat

<400> SEQUENCE: 26
gcggaattcc accatggagt gggtgtgggc                                            30

<210> SEQ ID NO 27
<211> LENGTH: 27
<212> TYPE: DNA
<213> ORGANISM: Artificial Sequence
<220> FEATURE:
<223> OTHER INFORMATION: antisense primer for RBP(1-585) in rat

<400> SEQUENCE: 27
cccctcgagt ctgctttgac agtaacc                                               27

<210> SEQ ID NO 28
<211> LENGTH: 32
<212> TYPE: DNA
<213> ORGANISM: Artificial Sequence
<220> FEATURE:
<223> OTHER INFORMATION: sense primer for albumin domain I in mouse

<400> SEQUENCE: 28
ggggtacccc accatgaagt gggtaacctt tc                                         32

<210> SEQ ID NO 29
<211> LENGTH: 27
<212> TYPE: DNA
<213> ORGANISM: Artificial Sequence
<220> FEATURE:
<223> OTHER INFORMATION: antisense primer for albumin domain I in mouse

<400> SEQUENCE: 29
ccccaattgc attctctgac ggacaga                                               27

<210> SEQ ID NO 30
<211> LENGTH: 27
<212> TYPE: DNA
<213> ORGANISM: Artificial Sequence
<220> FEATURE:
<223> OTHER INFORMATION: sense primer for albumin domain III in mouse

<400> SEQUENCE: 30
gggctcgagg aagagcctaa gaacttg                                               27

<210> SEQ ID NO 31
<211> LENGTH: 48
<212> TYPE: DNA
<213> ORGANISM: Artificial Sequence
<220> FEATURE:
<223> OTHER INFORMATION: antisense primer for albumin domain III in
```

```
        mouse

<400> SEQUENCE: 31
ggctctagat taatgatgat gatgatgatg ggctaaggtg tctttgca                    48

<210> SEQ ID NO 32
<211> LENGTH: 30
<212> TYPE: DNA
<213> ORGANISM: Artificial Sequence
<220> FEATURE:
<223> OTHER INFORMATION: sense primer for RBP(1-585) in mouse

<400> SEQUENCE: 32
gcggaattcc accatggagt gggtgtgggc                                       30

<210> SEQ ID NO 33
<211> LENGTH: 27
<212> TYPE: DNA
<213> ORGANISM: Artificial Sequence
<220> FEATURE:
<223> OTHER INFORMATION: antisense primer for RBP(1-585) in mouse

<400> SEQUENCE: 33
cccctcgagc ctgctttgac agtaacc                                          27

<210> SEQ ID NO 34
<211> LENGTH: 27
<212> TYPE: DNA
<213> ORGANISM: Artificial Sequence
<220> FEATURE:
<223> OTHER INFORMATION: sense primer for RBP(55-585) in mouse

<400> SEQUENCE: 34
gggcaattgg agcgcgactg cagggtg                                          27

<210> SEQ ID NO 35
<211> LENGTH: 27
<212> TYPE: DNA
<213> ORGANISM: Artificial Sequence
<220> FEATURE:
<223> OTHER INFORMATION: antisense primer for RBP(55-585) in mouse

<400> SEQUENCE: 35
cccctcgagc ctgctttgac agtaacc                                          27
```